United States Patent
Ziv et al.

(10) Patent No.: US 7,365,223 B2
(45) Date of Patent: Apr. 29, 2008

(54) METHOD FOR SELECTIVE TARGETING OF APOPTOTIC CELLS AND SMALL MOLECULE LIGANDS USED THEREOF

(75) Inventors: Ilan Ziv, Kfar Saba (IL); Anat Shirvan, Herzliya (IL)

(73) Assignee: NST NeuroSurvival Technologies Ltd, Petach-Tikva (IL)

( * ) Notice: Subject to any disclaimer, the term of this patent is extended or adjusted under 35 U.S.C. 154(b) by 190 days.

(21) Appl. No.: 10/560,747

(22) PCT Filed: Jun. 17, 2004

(86) PCT No.: PCT/IL2004/000535

§ 371 (c)(1),
(2), (4) Date: Dec. 15, 2005

(87) PCT Pub. No.: WO2004/110339

PCT Pub. Date: Dec. 23, 2004

(65) Prior Publication Data

US 2006/0160901 A1    Jul. 20, 2006

Related U.S. Application Data

(60) Provisional application No. 60/479,186, filed on Jun. 18, 2003, provisional application No. 60/491,292, filed on Jul. 31, 2003, provisional application No. 60/505,445, filed on Sep. 25, 2003, provisional application No. 60/523,115, filed on Nov. 19, 2003.

(51) Int. Cl.
*C07C 309/00*    (2006.01)
*C07C 307/02*    (2006.01)

(52) U.S. Cl. .................................... 562/427; 562/426

(58) Field of Classification Search .................... None
See application file for complete search history.

(56) References Cited

U.S. PATENT DOCUMENTS 5,876,956 A * 3/1999 Jones et al. .................. 435/26

OTHER PUBLICATIONS

Hua et al. Biochemistry, 1995, 34, 5137-5142.*
Abe et al. (Biochimica et Biophysica Acta 1999, 1433, 188-197).*

* cited by examiner

*Primary Examiner*—James O. Wilson
*Assistant Examiner*—Yevgeny Valenrod
(74) *Attorney, Agent, or Firm*—Pearl Cohen Zedek Latzer, LLP

(57) ABSTRACT

The invention provides novel methods for selective targeting of chemical compounds to cells undergoing a death process, in particular apoptosis, and to platelets undergoing activation during blood coagulation. The invention further provides compounds to be used in said methods for medical practice, for diagnostic and therapeutic purposes.

11 Claims, 11 Drawing Sheets

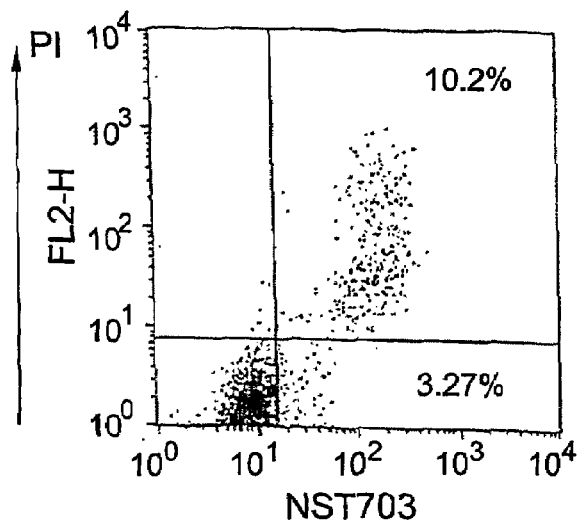
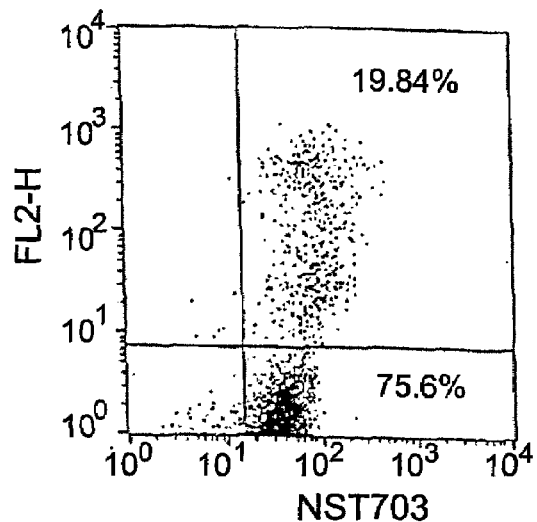
FIG. 2A  FIG. 2B
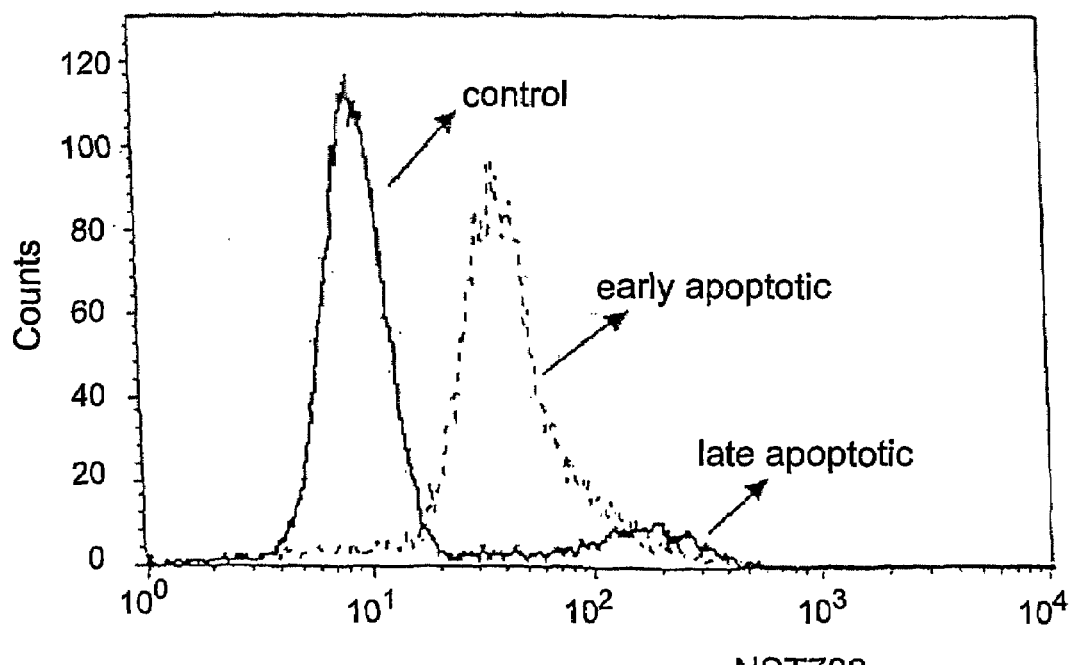
FIG. 2C

FIG. 3A
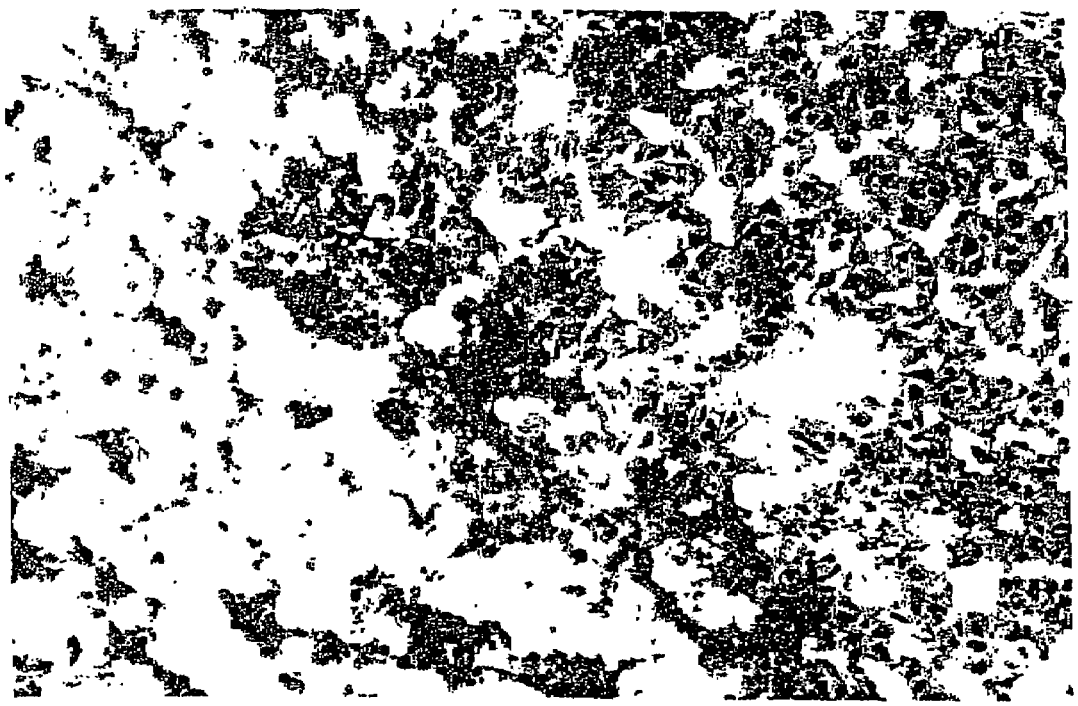
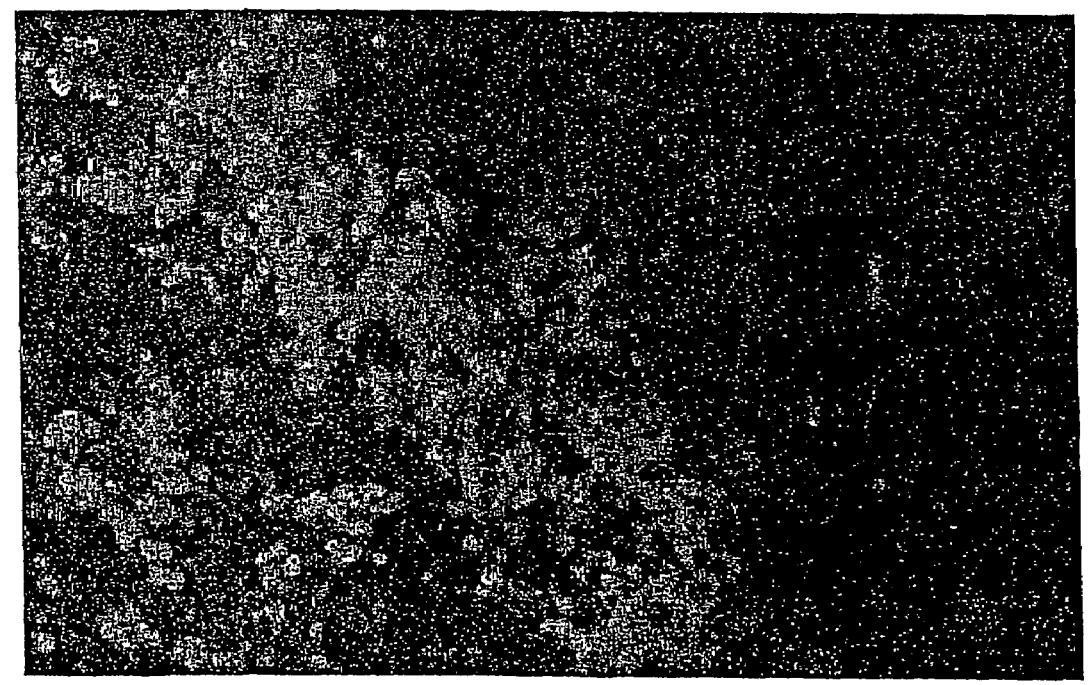
FIG. 3B

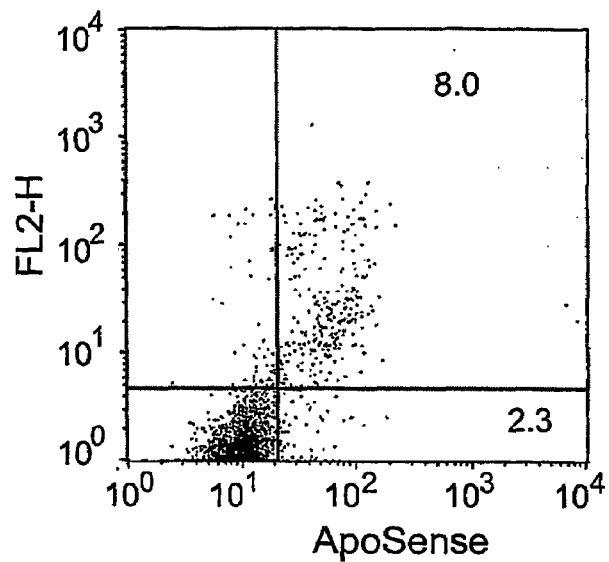
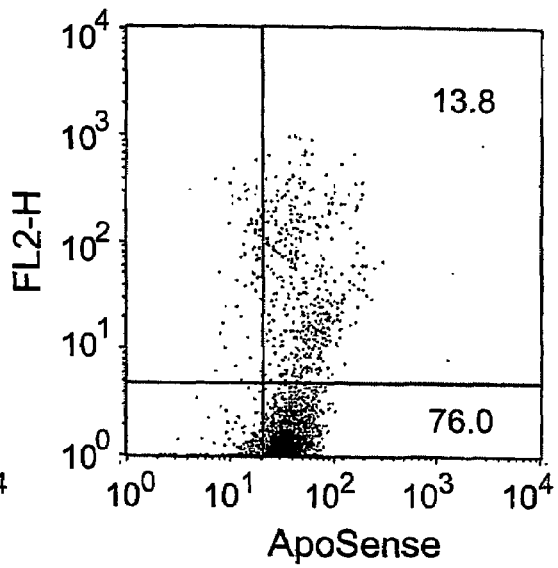
FIG. 4A  FIG. 4B
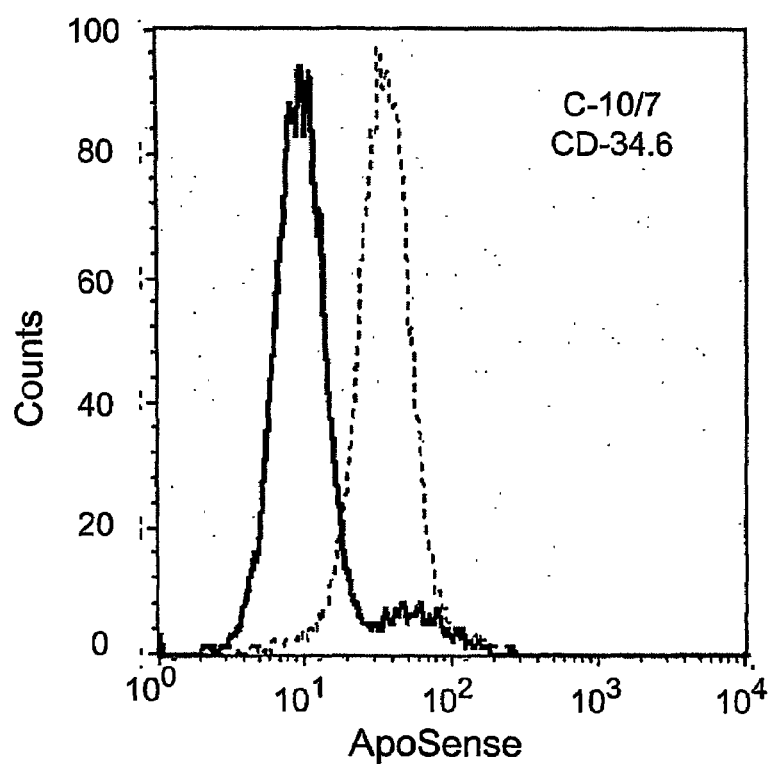
FIG. 4C

H&E

NST732

TUNEL

FIG. 11A
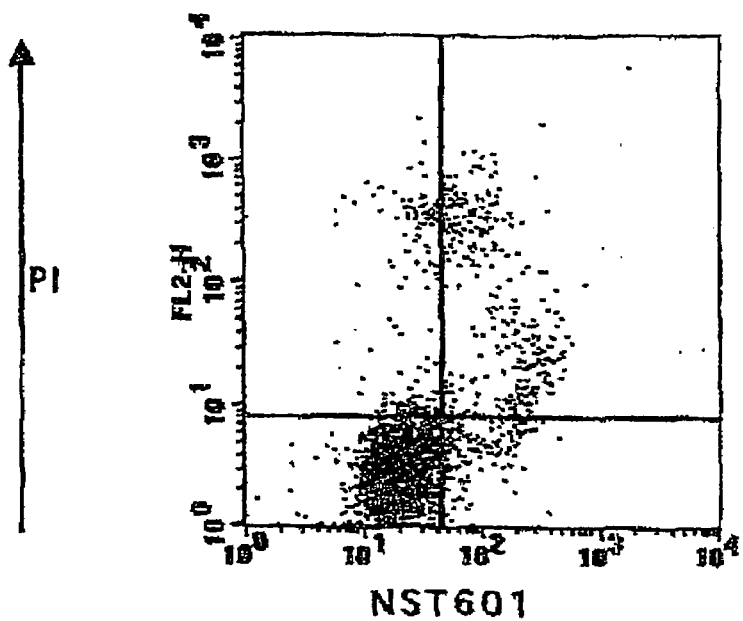
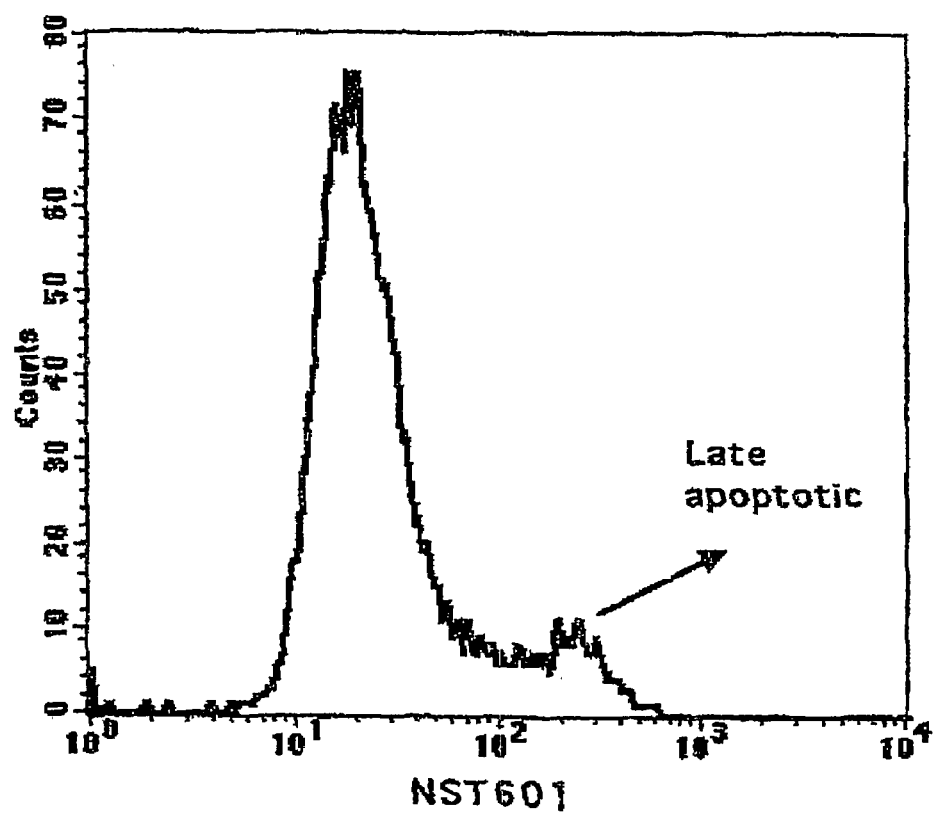
FIG. 11B

METHOD FOR SELECTIVE TARGETING OF APOPTOTIC CELLS AND SMALL MOLECULE LIGANDS USED THEREOF

PRIOR APPLICATION DATA

This application is a National Phase application of PCT International Application No. PCT/IL2004/000535, International Filing Date: Jun. 17, 2004, claiming priority from U.S. Provisional Patent Application Ser. No. 60/479,186, entitled "PERTURBED MEMBRANE-BINDING COMPOUNDS" filed Jun. 18, 2003; U.S. Provisional Patent Application Ser. No. 60/491,292, entitled "PERTURBED MEMBRANE-BINDING COMPOUNDS" filed Jul. 31, 2003; U.S. Provisional Patent Application Ser. No. 60/505,445, entitled "PERTURBED MEMBRANE-BINDING COMPOUNDS" filed Sep. 25, 2003 and U.S. Provisional Patent Application Ser. No. 60/523,115, entitled "PERTURBED MEMBRANE-BINDING COMPOUNDS" filed Nov. 19, 2003 all of which are incorporated by reference in their entirety.

FIELD OF THE INVENTION

The invention relates to novel methods for selective targeting of chemical compounds to cells undergoing a death process, in particular apoptosis, and to platelets undergoing activation during blood coagulation. The invention further provides small molecular weight compounds to be used for medical practice, namely, for diagnostic and therapeutic purposes.

BACKGROUND OF THE INVENTION

The plasma membrane (outer membrane) of intact eukaryotic cells is characterized by a highly organized structure. This high level of membrane organization is determined, among others, by the molecular structure of the is specific lipids constituting the membrane; the ratio between the various lipid species from which the membrane is composed; the distribution of the phospholipids between the outer and inner leaflets of the membrane; and by the membrane protein constituents.

While maintenance of the high level of membrane organization is fundamental to normal cell physiology, substantial perturbations and alterations of the normal organization of the cell plasma membrane (PNOM) occur in cells undergoing a death process, especially by apoptosis, and in platelets undergoing activation during blood coagulation. Such alterations and perturbations may be evident both at the morphological level (e.g., membrane blebbing) and at the molecular level. The scope of these perturbations occurring during cell death or platelet activation is not fully elucidated. They include, among others, scrambling and redistribution of the membrane phospholipids, with movement to the cell surface of aminophsopholipids, mainly phosphatidylserine (PS) and phosphatidylethanolamine (PE), which are normally restricted almost entirely to the inner leaflet of the membrane bilayer, and reciprocal movement of sphingomyelin (SM) and phosphatidylcholine (PC) from the outer leaflet to the inner leaflet of the membrane. PNOM is also often associated with reduction in the level of packing of membrane phospholipids and an increase in membrane fluidity.

These alterations play an important role in making the cell surface a catalytic platform for the assembly of several clotting factor complexes, such as the tenase and prothrombinase protein complexes. Thus, PNOM occurring in platelets upon constitutes an important factor in normal blood coagulation, as well as in the initiation and/or propagation of abnormal, excessive blood clotting in numerous disorders. These disorders include, among others, arterial or venous thrombosis or thrombo-embolism.

Apoptosis is another major situation in which PNOM takes place. Apoptosis is an intrinsic program of cell self-destruction or "suicide", which is inherent in every eukaryotic cell. In response to a triggering stimulus, cells undergo a highly characteristic cascade of events of cell shrinkage, blebbing of cell membranes, chromatin condensation and fragmentation, culminating in cell conversion to clusters of membrane-bound particles (apoptotic bodies), which are thereafter engulfed by macrophages. PNOM is a universal phenomenon in apoptosis, it occurs early in the apoptotic cascade, and has also been shown to be an important factor in the recognition and removal of apoptotic cells by macrophages.

Annexin V is a 37 kDa protein, capable of selective binding to apoptotic cells by binding to PS headgroups emerging on the surface of these cells as the result of the apoptosis-related PNOM process. However, annexin V is a relatively large protein, requiring relatively complex procedures of synthesis and marker attachment. Moreover, annexin V binds only to the surface of the cell in early apoptosis and can not perform accumulation within the cell at that stage.

It is therefore desirable to have small-molecular weight compounds, capable of selective targeting, binding and accumulation within cells undergoing PNOM (PNOM-cells). Such compounds can have applications in molecular imaging of apoptosis and blood clotting. Such compounds can also have useful therapeutic applications, when attached to therapeutically-useful drugs, by functioning as targeting moieties, enabling the active drug to target, bind and accumulate specifically in cells undergoing PNOM, thus allowing enhanced concentrations of the active drug in foci of disease.

SUMMARY OF THE INVENTION

In one embodiment of the invention there is provided a method for selective targeting of a chemical compound to a cell undergoing perturbation of the normal organization of its plasma membrane, selected from a cell undergoing a death process such as apoptosis, and a platelet undergoing activation. Collectively, these cells are designated hereinafter PNOM-cells. The method concerns selective targeting of the chemical compound to these cells being present or scattered within a cell population. The method comprises the steps of:

(i). contacting the cell population with a chemical compound, designated perturbed membrane binding compound (PMBC), or a conjugate comprising the PMBC. The PMBC is a compound represented by the structure set forth in formula (I):

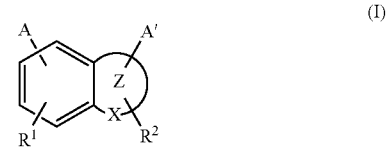

wherein Z represents null, or a ring system formed of cycloalkyl, cycloalkenyl, heterocyclyl, aryl or heteroaryl groups or combinations of such groups, the ring system consisting of 5, 6, 7, 8, 9 or 10 atoms;

X represents an atom, which is C, N, O or S, where each of these atoms may bear 0, 1 or 2 hydrogen atoms according to the meaning of Z;

$R^1$ and $R^2$ are each independently selected from hydrogen, halogen, hydroxyl, —$NO_2$ group or W-$Q_b$; wherein W is null, nitrogen, oxygen or carbon; and Q represents hydrogen, a $C_1$, $C_2$, $C_3$, $C_4$, $C_5$ or $C_6$ allyl, hydroxyalkyl, or straight or branched haloalkyl, wherein Q groups may be either the same or different; and b is an integer, being 1 when W is oxygen or null; 2 in the case that W is nitrogen; or 3 in the case that W is a carbon atom;

A and A' are each a radical, independently selected from one of the following four groups:

i) hydrogen;

ii) $SO_3H$, and L-$SO_3H$, wherein L stands for a $C_1$, $C_2$, $C_3$, $C_4$ or $C_5$ alkylene linker;

iii) a structure, set forth in formula II:

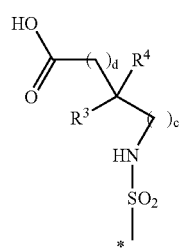

(II)

wherein $R^3$ is hydrogen, $(CH_2)_p$—OH, $(CH_2)_p$—SH, $(CH_2)_p$—F, or a radical of $C_1$, $C_2$, $C_3$, or $C_4$ carboxylic acid, wherein p is an integer of 1, 2, or 3;

$R^4$ is hydrogen, a $C_1$, $C_2$, $C_3$, $C_4$, $C_5$ $C_6$ straight or branched allyl, a $C_1$, $C_2$, $C_3$, $C_4$, $C_5$ $C_6$ straight or branched hydroxyalkyl or a $C_1$, $C_2$, $C_3$, $C_4$, $C_5$ $C_6$ straight or branched fluoroalkyl;

c and d are each an integer of 0 or 1; c and d may be the same or different;

* represents the point of attachment to the structure of formula (I); or iv) a structure set forth in formula (III):

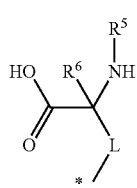

(III)

wherein $R^5$ and $R^6$ are independently hydrogen, straight or branched $C_1$, $C_2$, $C_3$, $C_4$, $C_5$, $C_6$ alkyl, straight or branched hydroxyalkyl and haloalkyl;

$R^5$ and $R^6$ can be the same or different; and L stands for null, or a $C_1$, $C_2$, $C_3$, $C_4$ or $C_5$ alkylene linker; * represents the point of attachment to the structure of formula (I);

at least one of A or A' groups is other than hydrogen, and other than the structure of formula (III);

thereby selectively targeting the chemical compound to the PNOM-cells within the cell population.

In another embodiment of the invention, there is provided a method of detecting the presence of PNOM-cells within a cell population suspected of comprising such a PNOM cell comprising the steps of: contacting the cell population with a PMBC, or a conjugate comprising the PMBC and a marker for imaging, wherein the PMBC is represented by the structure set forth in formula (I), wherein A, A', X, Z, $R^1$, $R^2$, $R^3$, $R^4$, $R^5$, $R^6$, L, c and d are as defined above; and (ii) determining the amount of PMBC bound to the cells, wherein a bound amount which is significantly higher than control indicates the presence of PNOM-cells within the cell population.

In another embodiment of the invention, there is provided a method for detecting the presence of PNOM-cells in a tissue of a patient or an animal, comprising the steps of: (i) administering a PMBC, or a conjugate comprising the PMBC and a marker for imaging to the human or the animal, wherein the PMBC is represented by the structure set forth in formula (I), wherein A, A', X, Z, $R^1$, $R^2$, $R^3$, $R^4$, $R^5$, $R^6$, L, c and d are as defined above; and (ii) determining the amount of PMBC bound to cells in the tissue, wherein an amount of compound bound to cells in a tissue which is significantly higher than the control indicates that the tissue contains PNOM-cells.

In an embodiment of the invention, the PNOM cell is in the body, organ, tissue, tissue culture or body fluid.

In another embodiment of the invention there is provided a compound represented by a structure as set forth in formula (V):

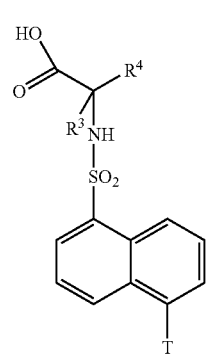

(V)

wherein T is —OH, —O—$CH_3$, —O—$(CH_2)_yCH_3$, $NH_2$, $N(CH_3)_2$, —N[$(CH_2)_3CH_3$]$_2$, —N($CH_3$)[$(CH_2)_2CH_3$], —N($CH_3$)$CH_2CH_3$ or —N($CH_3$)[$(CH_2)_3CH_3$]; y stands for an integer of 1, 2, or 3; and $R^3$, $R^4$ are each as defined above.

In another embodiment of the invention there is provided a compound represented by the structure as set forth in formula (VI):

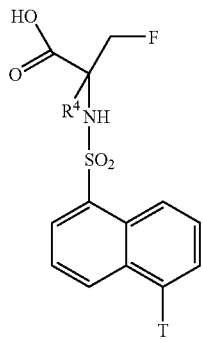

(VI)

wherein T is as defined above, and $R^4$ is hydrogen or a $C_1$, $C_2$, $C_3$, $C_4$, $C_5$ or $C_6$ alkyl, and wherein the F atom is $^{18}F$ or $^{19}F$.

In another embodiment of the invention, there is provided a compound represented by the structure as set forth in formula (VIII):

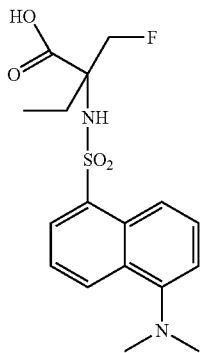

(VIII)

wherein the F atom is $^{18}F$ or $^{19}F$.

In another embodiment there is provided a method of selective targeting PNOM-cells, comprising the steps described above, using a compound represented by the structure as set forth in formula (XII):

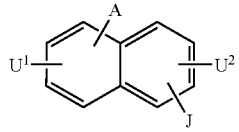

(XII)

wherein A is $SO_3H$ or $L\text{-}SO_3H$, wherein L stands for a substituted or unsubstituted $C_1$, $C_2$, $C_3$, $C_4$ or $C_5$ alkylene linker;

J is selected from A as defined above, hydrogen, and $W\text{-}Q_b$; wherein W is null, nitrogen, oxygen or carbon; and Q represents hydrogen, a $C_1$, $C_2$, $C_3$, $C_4$, $C_5$ or $C_6$ alkyl, hydroxyalkyl, or haloalkyl; wherein Q groups may be either the same or different; b is an integer, being 1 when W is oxygen or null, 2 in the case that W is nitrogen, or 3 in the case that W is a carbon atom;

$U^1$ and $U^2$ are each independently hydrogen, halogen, hydroxyl, $-NO_2$; $C_1$, $C_2$, $C_3$, $C_4$, $C_5$ or $C_6$ alkyl; $C_1$, $C_2$, $C_3$, $C_4$, $C_5$ or $C_6$ haloalkyl; $C_1$, $C_2$, $C_3$, $C_4$, $C_5$ or $C_6$ hydroxyalkyl; U groups may be the same or different.

The compounds of formula (XII) above may be considered to be within the scope of the broader formula (I) since the substituent J is similar to A' and the substituents $U^1$ and $U^2$ are similar to $R^1$ and $R^2$ in formula (I).

In another embodiment there is provided a method of detecting PNOM-cells in a population of cells, or in a tissue of a patient or an animal, comprising the steps described above, using a compound represented by the structure as set forth in formula (XII), comprising or being linked to a marker for imaging.

In another embodiment there is provided a method of selective targeting PNOM-cells, comprising the steps described above, using a compound represented by the structure as set forth in formula (XV):

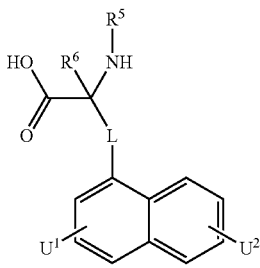

(XV)

wherein $R^5$ and $R^6$ are independently selected from hydrogen, $C_1$, $C_2$, $C_3$, $C_4$, $C_5$, $C_6$ straight or branched alkyl, straight or branched hydroxyalkyl or straight or branched fluoroalkyl; $R^5$ and $R^6$ can be the same or different;

L stands for null, or a $C_1$, $C_2$, $C_3$, C4 or $C_5$ alkylene linker, $U^1$ and $U^2$ are each independently hydrogen, halogen, hydroxyl, $-NO_2$; $C_1$, $C_2$, $C_3$, $C_4$, $C_5$ or $C_6$ straight or branched alkyl; $C_1$, $C_2$, $C_3$, $C_4$, $C_5$ or $C_6$ straight or branched haloalkyl; $C_1$, $C_2$, $C_3$, $C_4$, $C_5$ or $C_6$ straight or branched hydroxyalkyl; U groups may be the same or different.

In another embodiment there is provided a method of detecting PNOM-cells in a population of cells, or in a tissue of a patient or an animal, comprising the steps described above, using a compound represented by the structure as set forth in formula (XV), comprising or being linked to a marker for imaging.

In another embodiment of the invention, there is provided a method for labeling compounds described in the invention with a marker for PET imaging, the method comprising: attaching a marker for PET imaging to an amine subunit of the compound; and linking the amine subunit with a sulfonic acid subunit via formation of a sulfonamide bond.

In some embodiments of the invention, the marker for PET imaging may be $^{18}F$.

BRIEF DESCRIPTION OF THE DRAWINGS

FIG. 1: Selective binding of NST705 to Jurkat cells undergoing apoptosis induced by anti-Fas Ab; flow-cytometric analysis.

FIG. 2: Selective binding of NST703 to Jurkat cells undergoing apoptosis induced by anti-Fas Ab; flow-cytometric analysis; FIG. 2A and FIG. 2B are a FACS dot plot which describes the up-take of NST703 compound into the population of apoptotic cells in control and anti-Fas treated cultures, respectively. FIG. 2C is a histogram analysis of the data presented in FIGS. 2A and 2B.

FIGS. 3A, 3B: Fluorescence microscopy showing the selective binding of NST705 in vivo to tumor cells undergoing cell death; murine lymphoma.

FIG. 4: Selective binding of DC to cultured Jurkat cells undergoing apoptosis induced by anti-Fas Ab; flow-cytometric analysis; FIGS. 4A and 4B are dot plots showing the uptake of DC of control non-treated cells (4A) and cells upon induction of apoptosis (4B); FIG. 4C is a flow-cytometric (FACS) histogram representation of the data shown in FIG. 4A and 4B.

FIG. 5: Selective binding of DC in vivo to tumor cells undergoing cell death; B16 murine melanoma.

FIG. 6: Selective binding of NST730 to tumor cells undergoing cell death in vivo; B16 murine melanoma.

FIG. 10: Selective binding of NST601 to apoptotic HeLa cells; flow-cytometric analysis.

FIG. 11: Selective binding of DA to Jurkat cells undergoing apoptosis is induced by anti-Fas Ab; flow-cytometric analysis; FIG. 11A is a dot plot showing the selective binding upon induction of apoptosis; FIG. 11B is a histogram analysis of the data presented in FIG. 11A.

DETAILED DESCRIPTION OF THE EMBODIMENTS OF THE INVENTION

Figures 1A, 1B:
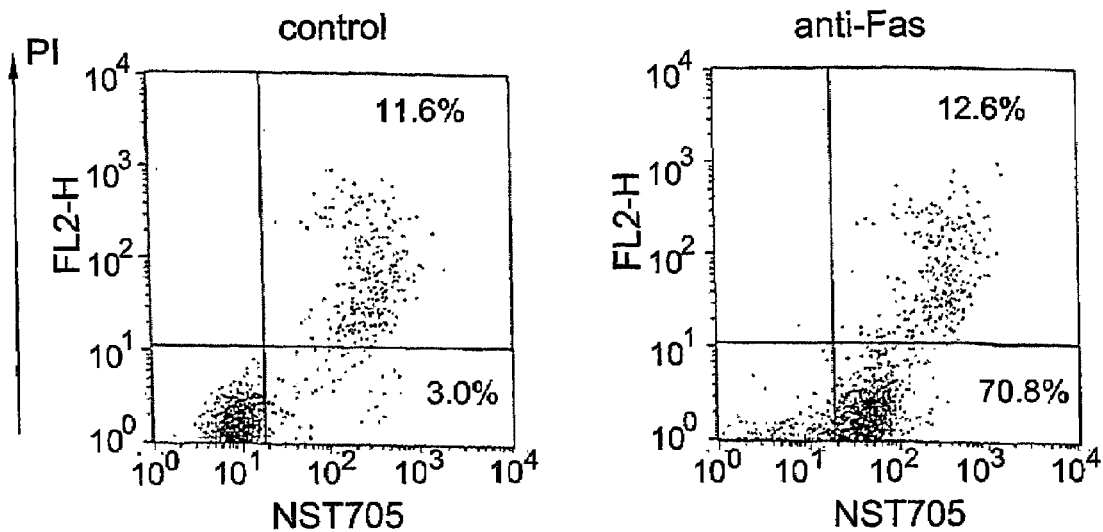
FIG. 1A and FIG. 1B are a FACS dot plot which describes the uptake of NST705 compound into the population of apoptotic cells in control and anti-Fas treated cultures, respectively.

In an embodiment of the invention, there is provided a compound and use thereof that selectively binds to cells undergoing perturbation of the normal organization of their plasma membrane, selected from cells undergoing a death process such as apoptosis, and platelets undergoing activation. Collectively, these cells are hereinafter designated PNOM-cells.

By contrast, the compound binds to a much lesser degree to cells which maintain the normal organization of their plasma membrane (normal cells). The ratio of binding is at least 30% higher in the PNOM-cell in comparison to a cell of the same tissue, which maintains the normal organization of its plasma membrane, and which is defined hereto as a "normal cell". The PNOM-cells are in one embodiment of the invention, cells undergoing a death process, in another embodiment they are apoptotic cells and in another embodiment they are activated platelets. The invention farther relates to methods of detecting PNOM-cells by using compounds that selectively bind to PNOM-cells.

The term "perturbed membrane-binding compound" (PMBC) refers to a compound that selectively targets PNOM-cells, while binding to a lesser degree to normal cells. According to the invention, binding of the PMBC to the PNOM-cell should be a least 30% greater than its binding to the normal cell. The compounds used in the invention, termed PMBC, include also pharmaceutically acceptable salts, metal chelates, solvates and hydrates of the compounds as well as solvates and hydrates of the pharmaceutically acceptable salts. Examples of pharmaceutically acceptable addition salts include inorganic and organic acid addition salts such as, for example without being limited, hydrochloride, hydrobromide, phosphate, sulphate, citrate, lactate, tartrate, maleate, fumarate, mandelate, oxalate, and acetate. Alternatively, pharmaceutically acceptable inorganic and organic base addition salts may be used such as sodium hydroxide, potassium hydroxide, lithium hydroxide, and the like.

The term "PMBC-Conjugate" or "Conjugate" means a PMBC, being linked to another useful compound, such as a marker for imaging or a drug.

The term "alkyl" or "alkylene" means a straight-chained or branched chain, optionally substituted alkyl or alkylene. Similarly, each of hydroxyalkyl and fluoroalkyl of the invention may be straight or branched.

The term "aryl" means a monocyclic or polycyclic aromatic ring system.

The term "Halogen" means fluorine, chlorine, bromine, or iodine;

Any of the alkyl, alkylene, aryl, and aralkyl of the invention may be substituted by one or more alkyl, nitro, halo, or hydroxy groups.

The term "selective targeting" refers in the invention to the selective binding of a PMBC to PNOM-cells, i.e., binding to the PNOM-cell in an extent which is at least 30% greater than binding to normal cells.

The term "significant amount" according to the invention means that the amount of PMBC bound to a PNOM-cell is at least 30% higher than the amount bound to a non-PNOM-cell. In another embodiment of the invention, the amount may be at least 50%. In another embodiment, the amount may be at least 60%. In another embodiment, the amount may be at least 70%. In another embodiment, the amount may be at least 80%. In another embodiment, the amount may be at least 90%. In another embodiment, the amount may be at least 95%. In another embodiment, the amount may be at least 150%. In another embodiment, the amount may be at least 200%. In another embodiment, the amount may be more than 5 times than the amount binding to a non PNOM-cell. The method for determining the actual amount may vary according to the imaging method and equipment utilized, and according to the organs or tissues examined.

The term "solid support" refers in the contents of the present invention to a solid matrix, an insoluble matrix, and an insoluble support. The solid support in accordance with the invention may be formed in a variety of structures such as a stack of micro-particulates, micro-filters, or micro-capillara, and may be composed of various materials such as alumina, diatomaceous earth, celite, calcium carbonate, calcium sulfate, ion-exchange resin, silica gel, charcoal, amberlite, Dowex, Eupergit and ethylsufoxycellulose.

The PMBC is used, in an embodiment of the invention, for the preparation of an agent for selective targeting of PNOM-cells in vivo or in vitro. Among others, the PMBC may be used for the preparation of an agent comprising a marker for imaging, for the detection of PNOM-cells in vivo or in vitro.

In an embodiment of the invention, the compounds of the invention may be linked to any one of the following agents or to combinations thereof, thus creating a "PMBC-Conjugate" or "Conjugate". The linkage can be either directly, or via a linker, wherein the linker is selected from a $C_1$, $C_2$, $C_3$, $C_4$, $C_5$ or $C_6$ alkylene, 5 or 6 atom aromatic or heteroaromatic ring, a metal chelator and combinations thereof, wherein the agents may be as follows:

i. Marker for imaging, selected from a detector of color, fluorescence, x-ray, CT scan, magnetic resonance imaging (MRI) and radio-isotope scan, such as single photon emission tomography (SPECT) or positron emission tomography (PET);

ii. A drug, for the prevention, amelioration or treatment of a specific disease which manifests occurrence of PNOM-cells. The drug may be, without being limited, any drug such as: (i) An inhibitor of apoptosis, (e.g., caspase inhibitor, antioxidant, modulator of the Bcl-2 system); (ii) An activator of cell death, an inducer of apoptosis (e.g., an anticancer drug); (iii) A modulator of blood coagulation, selected from an anticoagulant, an antithrombotic, or a thrombolytic agent. According to this embodiment the drug may be selected from an antiplatelet agent, heparin, low molecular weight heparin, antagonists of glycoprotein IIb/IIIa, tissue plasminogen activator (tPA), or an inhibitor of a clotting factor, such as an inhibitor of thrombin or an inhibitor of factor Xa; (iv) An anti-inflammatory drug or an immuno-modulator drug; or (v) Certain radioactive atoms may also be cytotoxic if delivered in sufficient doses.

iii. A solid support:

In an embodiment of the invention there is provided a method for selective targeting of a chemical compound to PNOM-cells. The method comprises the steps of: (i). contacting the cell population with a chemical compound, designated perturbed membrane binding compound (PMBC), or a conjugate comprising the PMBC. The PMBC is a compound represented by the structure set forth in formula (I):

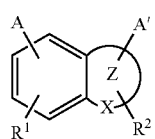

wherein Z represents null, or a ring system formed of cycloalkyl, cycloalkenyl, heterocyclyl, aryl or heteroaryl groups or combinations of such groups, the ring system consisting of 5, 6, 7, 8, 9 or 10 atoms;

X represents an atom, which is C, N, O or S, where each of these atoms may bear 0, 1 or 2 hydrogen atoms according to the meaning of Z;

$R^1$ and $R^2$ are each independently selected from hydrogen, halogen, hydroxyl, —$NO_2$ group or W-$Q_b$; wherein W is null, nitrogen, oxygen or carbon; and Q represents hydrogen, a $C_1$, $C_2$, $C_3$, $C_4$, $C_5$ or $C_6$ alkyl, hydroxyalkyl, or haloalkyl, wherein Q groups may be either the same or different; and b is an integer, being 1 when W is oxygen or null; 2 in the case that W is nitrogen; or 3 in the case that W is a carbon atom;

A and A' are each a radical selected from one of the following four groups:

i) hydrogen;

ii) $SO_3H$, and L-$SO_3H$, wherein L stands for a $C_1$, $C_2$, $C_3$, $C_4$ or $C_5$ alkylene linker;

iii) a structure, set forth in formula II:

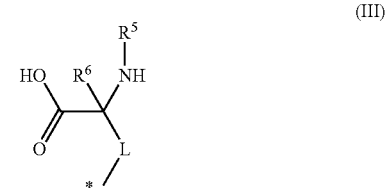

wherein $R^3$ is selected from hydrogen, $(CH_2)_p$—OH, $(CH_2)_p$—SH, $(CH_2)_p$—F, and a radical of $C_1$, $C_2$, $C_3$, or $C_4$ carboxylic acid, wherein p is an integer of 1, 2, or 3;

$R^4$ is hydrogen, a $C_1$, $C_2$, $C_3$, $C_4$, $C_5$ $C_6$ alkyl, a $C_1$, $C_2$, $C_3$, $C_4$, $C_5$ $C_6$ hydroxyalkyl or a $C_1$, $C_2$, $C_3$, $C_4$, $C_5$ $C_6$ fluoroalkyl;

c and d are each an integer of 0 or 1; c and d may be the same or different;

* represents the point of attachment to the structure of formula (I); or iv). a structure set forth in formula (III):

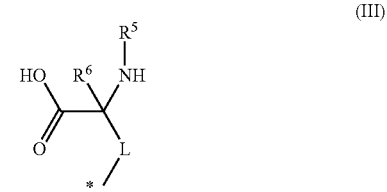

wherein $R^5$ and $R^6$ are independently selected from hydrogen, $C_1$, $C_2$, $C_3$, $C_4$, $C_5$, $C_6$ alkyl, hydroxy-alkyl and halo-allyl; $R^5$ and $R^6$ can be the same or different; and L stands for null, or a $C_1$, $C_2$, $C_3$, $C_4$ or $C_5$ alkylene linker; * represents the point of attachment to the structure of formula (I);

wherein at least one of A or A' groups is other than hydrogen, and other than the structure of formula (III);

(ii). thereby selectively targeting the chemical compound to the PNOM-cells within the cell population.

In an embodiment of the invention, the PNOM-cell is a cell undergoing a death process, an apoptotic cell or an activated platelet.

In an embodiment of the invention the PNOM cell may be targeted in the body, organ, tissue, tissue culture or body fluid.

The ability of the compounds of the invention to selectively bind to cells undergoing apoptosis is shown in Examples 3-7, 9-12 and 15-16 and in FIGS. 1-11, which are all directed to the ability of the compounds of the invention to bind to cells undergoing apoptosis under in-vitro and in-vitro conditions.

In accordance some embodiments of the invention, the invention may be used for the detection of PNOM-cells. According to this approach, there is provided use of a composition comprising PMBC or a PMBC-Conjugate as defined above, which comprises a marker for imaging, for the detection of PNOM-cells in a sample either in vitro, ex vivo or in vivo and a pharmaceutically acceptable carrier.

In another embodiment of the invention, there is provided a method of detection of the presence of PNOM-cells within a cell population, suspected of comprising such a PNOM cell, comprising the steps of: (i). contacting the cell population with a PMBC, or a conjugate comprising the PMBC and a marker for imaging, wherein the PMBC is represented by the structure set forth in formula (I), wherein A, A', X, Z, $R^1$, $R^2$, $R^3$, $R^4$, $R^5$, $R^6$, L, c and d are as defined above; and (ii). determining the amount of PMBC bound to the cells, wherein a bound amount which is significantly higher than control indicates the presence of PNOM-cells within the cell population.

In another embodiment of the invention, there is provided a method for detecting the presence of PNOM-cells in a tissue of a patient or an animal, comprising the steps of: (i). administering a PMBC, or a conjugate comprising the PMBC and a marker for imaging to the human or the animal, wherein the PMBC is represented by the structure set forth in formula (I), wherein A, A', X, Z, $R^1$, $R^2$, $R^3$, $R^4$, $R^5$, $R^6$, L, c and d are as defined above; and (ii). determining the amount of PMBC bound to cells in the tissue, wherein an amount of compound bound to cells in a tissue which is significantly higher than the control indicates that the tissue contains PNOM-cells.

In an embodiment of the invention, the PNOM cell is in the body, organ, tissue, tissue culture or body fluid.

The term "control" refers in an embodiment of the invention to the amount of the compound that binds to a normal cell. A normal cell for the purpose of the invention means a cell from the same tissue, or the same sample, which maintains the normal organization of its plasma membrane.

The term "marker for imaging" refers to any reporter molecule including radionuclides, enzymes, fluorescent, chemiluminescent, or chromogenic agents, substrates, cofactors, inhibitors, or magnetic particles, a label capable of undergoing an enzymatic reaction producing a detectable color, a marker for x-ray, a marker for MRI or a marker for radio-isotope imaging, such as single photon emission tomography (SPECT), CT scan, MRI or positron emission tomography (PET scan). The PMBC or a PMBC-Conjugate of the invention enables the targeting of the marker, through the action of the PMBC, to PNOM-cells in a selective manner. Then, the detectable label can be detected by any manner known in the art, and in accordance with the specific label used, for example, fluorescence, radioactive emission, or a color production, MRI, x-ray and the like. The term "bound" refers to covalent or non-covalent (e.g., electrostatic) binding, which connects the PNOM to the detectable label.

In an embodiment of the invention, the detectable label may be any of the following metal isotopes Tc, In, Cu, Ga, Xe, Tl and Re and the covalently linked atoms: $^{123}$I and $^{131}$I for radio-isotope scan, gadolinium(III), terbium(III), dysoprosium(III), holmium(III), erbium(III), chromium(III), manganese(II), iron(III), iron(II), cobalt(II), nickel(II), copper(II), praseodymium(III), neodymium(III), samarium(III) and ytterbium(III) for MRI and $^{18}$F, $^{15}$O, $^{18}$O, $^{11}$C, $^{13}$C, $^{124}$I, $^{13}$N and $^{75}$Br for Positron Emission Tomography (PET) scan.

In an embodiment of the invention, the PMBC or the PMBC-Conjugate is aimed at clinical imaging of apoptosis or blood clots via PET scan. In such case, the PMBC or a PMBC-Conjugate may comprise in an embodiment of the invention, a marker for PET imaging, imaging such as, for example in some embodiments of the invention, $^{18}$F atom(s), being linked to the PMBC either directly or through linker as defined above.

Since the radio-label for PET often has a relatively short half-life (e.g., 115 minutes for $^{18}$F), the attachment of the radio-isotope is often done as the last step of the synthesis, immediately before the administration of the diagnostic compound to the patient. Therefore, it may be advisable to synthesize a PMBC-PET precursor, being a PMBC, comprising or attached to a moiety to be substituted by $^{18}$F at the final step before imaging. In an embodiment of the invention, the moiety is a hydroxyl group, a nitro group, or a halogen atom such as bromine or chlorine. Such a PMBC-PET precursor is also included in the scope of the invention.

In another embodiment there is provided a method of selective targeting PNOM-cells, comprising the steps described above, using a compound represented by the structure as set forth in formula (IV):

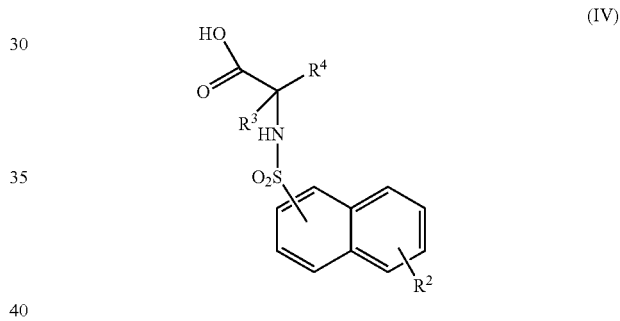

wherein $R^2$, $R^3$ and $R^4$ are as defined formula I.

In another embodiment there is provided a method of detecting PNOM-cells in a population of cells, or in a tissue of a patient or an animal, comprising the steps described above, using a compound represented by the structure as set forth in formula (IV), comprising or being linked to a marker for imaging, wherein $R^2$, $R^3$ and $R^4$ are as was previously defined in formula I.

In another embodiment of the invention there is provided a compound represented by a structure as set forth in formula (V):

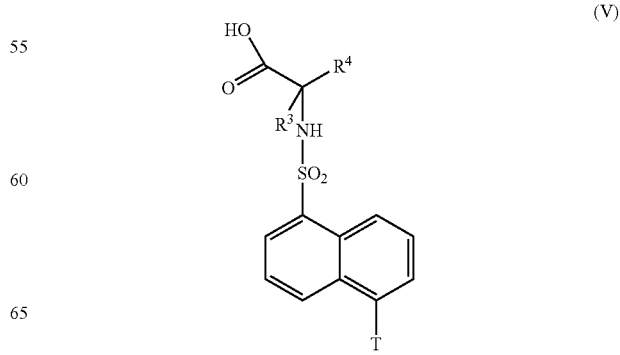

wherein T is —OH, —O—CH₃, —O—(CH₂)ᵧCH₃, NH₂, N(CH₃)₂, —N[(CH₂)₃CH₃]₂, —N(CH₃)[(CH₂)₂CH₃], —N(CH₃)CH₂(CH₃ or —N(CH₃)[(CH₂)₃CH₃]; y stands for an integer of 1, 2, or 3; and $R^3$, $R^4$ are each as defined above.

In another embodiment of the invention there is provided a compound represented by the structure as set forth in formula (VI):

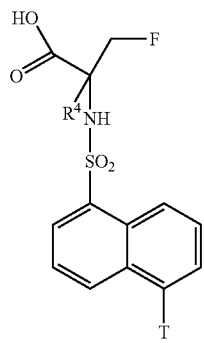

(VI)

wherein T is as defined above, and $R^4$ is hydrogen or a $C_1$, $C_2$, $C_3$, $C_4$, $C_5$ or $C_6$ alkyl, and wherein the F atom is $^{18}$F or $^{19}$F or a mixtures of isotopes.

In another embodiment of the invention, there is provided a compound, designated NST730, represented by the structure as set forth in formula (VII):

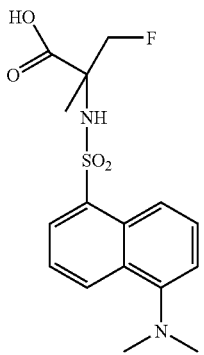

(VII)

wherein the F atom is $^{18}$F or $^{19}$F or a mixtures of isotopes.

In another embodiment, there is provided a compound, designated NST732, represented by the structure as set forth in formula (VIII):

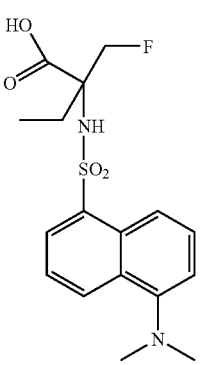

(VIII)

wherein the F atom is $^{18}$F or $^{19}$F or a mixtures of isotopes.

In another embodiment, there is provided a compound, designated NST705, represented by the structure as set forth in formula (IX):

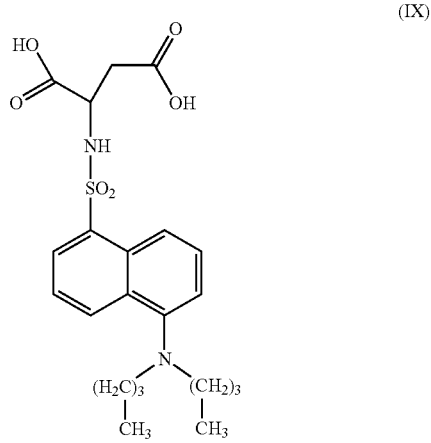

(IX)

In another embodiment, there is provided a compound, designated NST703, represented by the structure as set forth in formula (X):

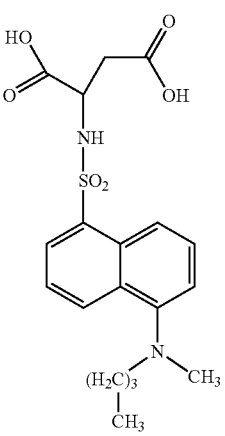

(X)

In another embodiment, there is provided a compound represented by the structure as set forth in formula (XI):

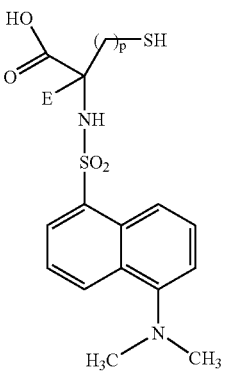

(XI)

wherein E is hydrogen; $C_1$, $C_2$, $C_3$ or $C_4$ alkyl; $C_1$, $C_2$, $C_3$ or $C_4$ fluoroalkyl; or $C_1$, $C_2$ $C_3$ or $C_4$ hydroxyalkyl; p stands for an integer of 1 or 2.

In the case that E is hydrogen and p is 1, the compound is dansylcysteine (DC). It should be noted that DC is a known compound in the art. However, its use as a PMBC, which selectively bind to PNOM-cells, and its use for the detection of PNOM-cells in vitro or in vivo is novel.

In another embodiment of the invention there is provided a compound represented by the structure as set forth in formula XI, wherein E is selected from $C_1$, $C_2$, $C_3$ or $C_4$ alkyl; $C_1$, $C_2$, $C_3$ or $C_4$ fluoroalkyl; and $C_1$, $C_2$, $C_3$ or $C_4$ hydroxyalkyl and p is 1 or 2.

In another embodiment there is provided a method of selective targeting PNOM-cells, comprising the steps described above, using a compound represented by the structure as set forth in formula (XII):

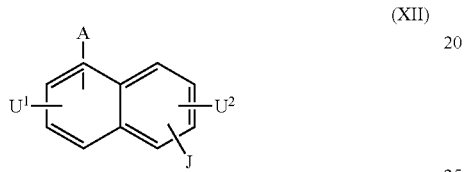

(XII)

wherein A is $SO_3H$ or $L-SO_3H$, wherein L stands for a substituted or unsubstituted $C_1$, $C_2$, $C_3$, $C_4$ or $C_5$ alkylene linker;

J is selected from A as defined above, hydrogen, and $W-Q_b$; wherein W is null, nitrogen, oxygen or carbon; and Q represents hydrogen, a $C_1$, $C_2$, $C_3$, $C_4$, $C_5$ or $C_6$ alkyl, hydroxyalkyl, or haloalkyl; wherein Q groups may be either the same or different; b is an integer, being 1 when W is oxygen or null, 2 in the case that W is nitrogen, or 3 in the case that W is a carbon atom;

$U^1$ and $U^2$ are each hydrogen, halogen, hydroxyl, $-NO_2$; $C_1$, $C_2$, $C_3$, $C_4$, $C_5$ or $C_6$ alkyl; $C_1$, $C_2$, $C_3$, $C_4$, $C_5$ or $C_6$ halo-alkyl; $C_1$, $C_2$, $C_3$, $C_4$, $C_5$ or $C_6$ hydroxy-alkyl; U groups may be the same or different.

In another embodiment there is provided a method of detecting PNOM-cells in a population of cells, or in a tissue of a patient or an animal, comprising the steps described above, using a compound represented by the structure as set forth in formula (XII), comprising or being linked to a marker for imaging.

In another embodiment of the invention, there is provided a compound represented by the structure as set forth in formula (XII), wherein either $U^1$ or $U^2$ is selected from fluorine, and $C_1$, $C_2$, $C_3$ or $C_4$ fluoroalkyl, the F atom being either $^{18}F$ or $^{19}F$ or a mixtures of isotopes.

In another embodiment there is provided a method of selective targeting PNOM-cells, comprising the steps described above using a compound represented by the structure as set forth in formula (XIII):

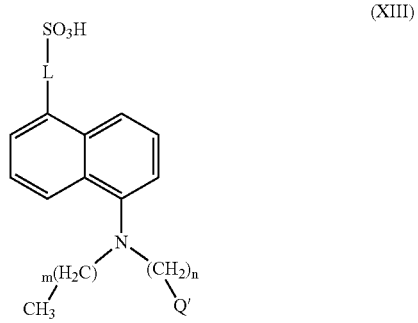

(XIII)

wherein n stands for an integer of 1, 2, 3, 4, 5 or 6, m stands for an integer of 0, 1, 2 or 3 and Q' is hydrogen, —OH or —F; L stands for null or a $C_1$, $C_2$, $C_3$, $C_4$ or $C_5$ alkylene linker.

In another embodiment there is provided a method of detecting PNOM-cells in a population of cells, or in a tissue of a patient or an animal, comprising the steps described above, using a compound represented by the structure as set forth in formula (XIII), comprising or being linked to a marker for imaging.

In another embodiment there is provided a method of selective targeting PNOM-cells, comprising the steps described above using a compound represented by the structure as set forth in formula (XIV):

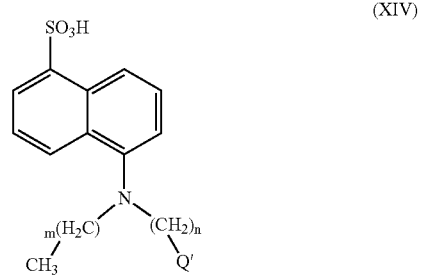

(XIV)

wherein n stands for an integer of 1, 2, 3, 4, 5 or 6, m stands for an integer of 0, 1, 2 or 3 and Q' stands for hydrogen, —OH or —F.

In another embodiment there is provided a method of detecting PNOM-cells in a population of cells, or in a tissue of a patient or an animal, comprising the steps described above, using a compound represented by the structure as set forth in formula (XIV), comprising or being linked to a marker for imaging.

In another embodiment, there is provided a compound represented by the structure as set forth in formula (XIV), wherein Q' is F, being either $^{18}F$ or $^{19}F$ or a mixtures of isotopes. In the case that m is 0, n is 4 and Q' is hydrogen, the compound is designated NST601.

In the case that m is 0, n is 3 and Q' is hydroxyl, the compound is designated NST602.

In the case that m is 0, n is 4 and Q' is fluorine, the compound is designated NST603.

In the case that m is 0, n is 1 and Q' is hydrogen, the compound is dansylic acid (DA). Dansylic acid is a known compound in the art, however, its use in the invention as a compound which selectively targets PNOM-cells, and it use for detection of PNOM-cells either in vitro or in vivo is novel.

In another embodiment there is provided a method of selective targeting PNOM-cells, comprising the steps described above, using a compound represented by the structure as set forth in formula (XV):

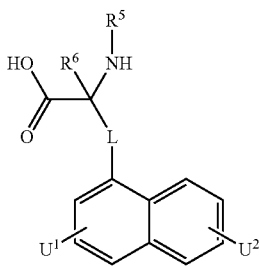

(XV)

wherein $R^5$ and $R^6$ are independently selected from hydrogen, $C_1$, $C_2$, $C_3$, $C_4$, $C_5$, $C_6$ straight or branched alkyl, straight or branched hydroxyalkyl or straight or branched fluoroalkyl; $R^5$ and $R^6$ can be the same or different;

L stands for null or a $C_1$, $C_2$, $C_3$, C4 or $C_5$ alkylene linker;

$U^1$ and $U^2$ are each hydrogen, halogen, hydroxyl, —$NO_2$; $C_1$, $C_2$, $C_3$, $C_4$, $C_5$ or $C_6$ straight or branched alkyl; $C_1$, $C_2$, $C_3$, $C_4$, $C_5$ or $C_6$ straight or branched haloalkyl; $C_1$, $C_2$, $C_3$, $C_4$, $C_5$ or $C_6$ straight or branched hydroxyalkyl; U groups may be the same or different.

In another embodiment, there is provided a method of detecting PNOM-cells in a population of cells, or in a tissue of a patient or an animal, comprising the steps described above, using a compound represented by the structure as set forth in formula (XV), comprising or being linked to a marker for imaging.

In another embodiment, there is provided a compound represented by the structure as set forth in formula (XV), wherein either $U^1$ or $U^2$ is selected from fluorine, and $C_1$, $C_2$, $C_3$ or $C_4$ fluoroalkyl, the F atom being either $^{18}F$ or $^{19}F$ or a mixtures of isotopes.

In another embodiment there is provided a method of selective targeting PNOM-cells, comprising the steps described above, using a compound represented by the structure as set forth in formula (XVI):

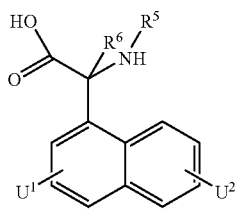

(XVI)

wherein $R^5$ and $R^6$ are independently selected from hydrogen, $C_1$, $C_2$, $C_3$, $C_4$, $C_5$, $C_6$ straight or branched allyl, straight or branched hydroxyalkyl or straight or branched fluoroalkyl; $R^5$ and $R^6$ can be the same or different; $U^1$ and $U^2$ are each hydrogen, halogen, hydroxyl, —$NO_2$; $C_1$, $C_2$, $C_3$, $C_4$, $C_5$ or $C_6$ alkyl; $C_1$, $C_2$, $C_3$, $C_4$, $C_5$ or $C_6$ haloalkyl; $C_1$, $C_2$, $C_3$, $C_4$, $C_5$ or $C_6$ hydroxyalkyl; U groups may be the same or different.

In another embodiment, there is provided a method of detecting PNOM-cells in a population of cells, or in a tissue of a patient or an animal, comprising the steps described above, using a compound represented by the structure as set forth in formula (XVI), comprising or being linked to a marker for imaging.

In another embodiment, there is provided a compound represented by the structure as set forth in formula (XVI), wherein $R^5$ is $C_1$, $C_2$, $C_3$, $C_4$, $C_5$, $C_6$ straight or branched alkyl, straight or branched hydroxyalkyl or straight or branched fluoroalkyl; $R^6$ is $C_2$, $C_3$, $C_4$, $C_5$, $C_6$ straight or branched alkyl, straight or branched hydroxyalkyl or straight or branched fluoroalkyl; and either $U^1$ or $U^2$ is other than hydrogen.

In the case that both U groups are hydrogen atoms, $R^5$ is butyl and $R^6$ is hydrogen, the compound is designated NST 650.

In the case that one of the U groups is fluorine, being either $F^{18}$ or $F^{19}$, $R^5$ is butyl and $R^6$ is hydrogen, the compound is designated NST 651.

In the case that both U groups are hydrogen atoms, $R^5$ is butyl and $R^6$ is methyl, the compound is designated NST 652.

In the case that one of the U groups is fluorine, being either $F^{18}$ or $F^{19}$, $R^5$ is butyl and $R^6$ is methyl, the compound is designated NST 653.

In the case that both U groups are hydrogen atoms, $R^5$ is hydrogen and $R^6$ is butyl, the compound is designated NST 654.

In the case that one of the U groups is fluorine, being either $F^{18}$ or $F^{19}$, $R^5$ is hydrogen and $R^6$ is butyl, the compound is designated NST 655.

In another embodiment there is provided a method of selective targeting a compound to PNOM cells, the method comprising the steps described above, by using a compound represented by the structure as set forth in any of formulae I, IV, V, VI, VII, VIII, IX, X, XI, XII, XIII, XIV, XV or XVI.

In another embodiment there is provided a method of detecting PNOM cells in a population of cells comprising the steps described above, with a compound represented by the structure as set forth in any one of formulae I, IV, V, VI, VII, VIII, IX, X, XI, XII, XII, XIV, XV or XVI.

In another embodiment there is provided a method of detecting by imaging the presence of PNOM-cells in a tissue in a patient or an animal, comprising the steps described above, with compound represented by the structure as set forth in any one of formulae I, IV, V, VI, VII, VIII, IX, X, XI, XII, XIII, XIV, XV, or XVI.

In another embodiment there is provided use of a compound represented by the structure as set forth in any of formulae I, IV, V, VI, VII, VIII, IX, X, XI, XII, XIII, XIV, XV or XVI for selective targeting a compound to PNOM cells.

In another embodiment there is provided use of a compound represented by the structure as set forth in any of formulae I, IV, V, VI, VII, VIII, IX, X, XI, XII, XIII, XIV, XV or XVI for detecting PNOM cells.

In another embodiment there is provided a compound represented by the structure as set forth in any of formulae I, IV, V, VI, VII, VIII, IX, X, XI, XII, XIII, XIV, XV or XVI for detecting by imaging the presence of PNOM-cells in a tissue in a patient or an animal.

In an embodiment, the invention provides a method of detecting a PNOM-cell in the brain of an examined subject, the method comprising: (i) administering to the examined subject a compound according to the structure set forth in any one of formulae I, IV, V, VI, VII, VIII, IX, X, XI, XII, XIII, XIV, XV or XVI, wherein the compound comprises or is linked to a marker for imaging or a labeled metal chelate; and (ii) determining the amount of the compound bound to cells in the brain, wherein a significant amount of the compound bound to a cell indicates its being a PNOM-cell. The ability of the PMBC of the invention to detect PNOM cells in the brain is demonstrated in Examples 11 and 12 and in FIGS. 8 and 9.

In another embodiment, the invention provides a method of detecting cells undergoing a death process within a tumor in an examined subject, the method comprising: administering to the examined subject a compound or a conjugate comprising the compound and a marker for imaging, wherein the compound is represented by the structure set forth in any one of formulae I, IV, V, VI, VII, VIII, IX, X, XI, XII, XIII, XIV, XV or XVI; and imaging the examined subject according to the embodiments of the invention. This ability of the PMBC is demonstrated in different murine cancers such as lymphoma and melanoma (see Examples and FIGS. 3, 5, 6 and 7).

In some embodiments of the invention, there is provided an agent which may comprise each of the compounds provided in the invention linked either directly or through a linker Y to a member selected from a solid support, a marker for imaging or a therapeutic drug, wherein the linker Y is selected from a $C_1$, $C_2$, $C_3$, $C_4$, $C_5$ and $C_6$ alkylene; 5-6 atom aromatic or heteroaromatic ring, wherein the heteroatom of the heteroaromatic ring is N, O or S; a metal chelator, and combinations thereof.

In another embodiment of the invention, there is provided a method for attachment of a radio-marker for PET imaging, which can be in one embodiment without limitation an $^{18}F$ atom, to PMBC of the invention, having the structure set forth in Formula I, wherein A has the structure set forth in Formula II. The PMBC may be by regarded as consisting of two subunits as presented in the following scheme:

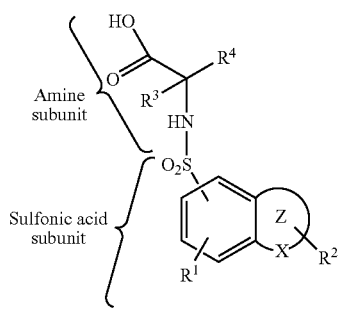

In such case, the attachment of the marker for PET imaging to the compound may comprise the following steps: (i) attaching the marker, e.g., the $^{18}F$ atom, to the amine subunit of the PMBC; and (ii). subsequent linking the radio-labeled amine subunit to the sulfonic acid subunit via formation of a sulfonamide bond.

In another embodiment of the invention, the method for labeling a PMBC with a marker for PET imaging, which can be in one embodiment without limitation $^{18}F$, further comprises the step(s) of protecting the functional groups of the amine subunit and/or the sulfonic acid subunit by appropriate protecting groups. In another embodiment, the protecting groups are removed after the step of attaching the marker for PET imaging and/or after the step of linking the amine subunit with the sulfonic acid subunit. In another embodiment, the method further comprises a final step of product purification, by any method known to those in the art.

In an embodiment of the invention, wherein the marker for imaging is a metal atom (e.g., Gd or $^{99m}Tc$), the PMBC-Conjugate comprises a metal chelator. In an embodiment of the invention, the metal coordinating atoms of the chelator are selected from nitrogen, sulfur and oxygen atoms. In another embodiment of the invention, the chelator is selected from diaminedithiols, monoamine-monoamide-bisthiols (MAMA), triamide-monothiols, and monoamine-diamide-monothiols.

In such case, both the PMBC-Conjugate Precursor, being the PMBC attached to the chelator prior to complexation with the metal atom, and the complex comprising the metal atom are included in the scope of the invention.

In the case that the marker for imaging comprised within the PMBC or the PMBC-Conjugate is a fluorescence-emitting moiety, the moiety may be a 5-(dimethylamino) naphthalene-1-sulfonylamide (dansyl-amide) group, linked to the PMBC either directly or via a linker as defined above.

The compounds and the methods of the invention may be used for a detection, diagnosis and for targeting pharmaceutically useful drugs to a foci of PNOM-cells, for a wide variety of physiological conditions, pathological conditions, diseases or disorders which are characterized by occurrence of PNOM-cells.

Examples of medical disorders characterized by PNOM-cells are, without being limited, as follows:

Diseases which are characterized by occurrence of excessive apoptosis, such as degenerative disorders, neurodegenerative disorders (e.g., Parkinson's disease, Alzheimer's disease, Huntington chorea), AIDS, myelodysplastic syndromes, ischemic or toxic insults, graft cell loss during transplant rejection; tumors, and especially highly malignant/aggressive tumors, are also often characterized by enhanced apoptosis, in addition to the excessive tissue proliferation. By way of such an example, the medical disorder can be cancer such as a central nervous system tumor, breast cancer, liver cancer, lung cancer, lymphoma, or melanoma.

Diseases manifested by excessive blood clotting: these diseases include, among others, arterial or venous thrombosis, thrombo-embolism, e.g., myocardial infarction, cerebral stroke, deep vein thrombosis, disseminated intravascular coagulation (DIC), thrombotic thrombocytopenic purpura (TTP), sickle cell diseases, thalassemia, antiphospholipid antibody syndrome, systemic lupus erythematosus.

Inflammatory disorders, and/or diseases associated with immune-mediated etiology or pathogenesis, auto-immune disorders such as antiphospholipid antibody syndrome, systemic lupus erythematosus, connective tissue disorders such as rheumatoid arthritis, scleroderma; thyroiditis; dermatological disorders such as pemphigus or erythema nodosum; autoimmune hematological disorders; autoimmune neurological disorders such as myasthenia gravis; multiple sclerosis; inflammatory bowel disorders such as ulcerative colitis; vasculitis.

Atherosclerotic plaques, and especially plaques that are unstable, vulnerable and prone to rupture, are also characterized by PNOM-cells, such as apoptotic macrophages, apoptotic smooth muscle cells, apoptotic endothelial cells and activated platelets.

The ability of the compounds of the invention to detect pathological conditions associated with cancer is demonstrated in Example 7 that shows targeting of DC to apoptotic cells in a tumor that was induced in mice.

The detection method may also be carried out to evaluate the severity of a related disease and in order to monitor response of the subject to a therapeutic agent. An example for such monitoring is evaluation of response to anticancer therapy. As can be clearly seen from Example 5, the compounds of the invention are able to detect chemotherapy-induced apoptosis of lymphoma cells. Since most anti-tumor treatments, chemotherapy or radiotherapy exert their effect by induction of apoptosis, detection by a PMBC of therapy-induced apoptosis of tumor cells may teach on the extent of sensitivity of a tumor to the anti-tumor agent shortly after treatment, before the occurrence of tumor shrinkage, thus substantially shortening the lag period between the time of administration of the anti-cancer treatment and the time of proper assessment of its efficacy. Moreover, such monitoring can be performed non-invasively and quantitatively, and can be repeated at intervals during the cancer therapy, thus providing valuable data on the temporal profile of the tumor response to the anti-cancer therapy.

In addition, the detection may be also used to monitor adverse effects of anti-cancer treatments. A large part of such adverse effects are due to untoward treatment-induced apoptosis of normal, yet sensitive cells, such as those of the gastrointestinal epithelium or the bone marrow hematopoietic system. Detection by the PMBC or a PMBC-Conjugate of apoptosis in such tissues may allow early detection of such untoward tissue damage and better optimization of the treatment protocol.

In addition, the detection method may aim at characterization of the intrinsic apoptotic load within a tumor, i.e., the level of spontaneous apoptosis occurring within the tumor. The apoptotic load often correlates with the level of tumor aggressiveness, and thus the method of the invention may provide valuable information for tumor characterization. The detection method may also assist in the detection of metastases, via detection of apoptosis within the metastases.

Similarly, PMBC or a PMBC-Conjugate of the current invention may be useful in monitoring graft survival after organ transplantation, since apoptosis, which may be detectable by the PMBC or the PMBC-Conjugate, plays a major role in cell loss during graft rejection.

In addition, the detection approach may be used for monitoring response to cyto-protective treatments, and accordingly may be used in screening and development of drugs which are capable of inhibiting cell loss in various diseases (for example those recited above) by enabling a measure of evaluation of cell death.

The detection may be also useful for the detection of atherosclerotic plaques, since destabilization of such plaques, rendering them vulnerable, prone to rupture, thrombosis and embolization, is characterized by participation of several types of PNOM-cells, including apoptotic cells (apoptotic macrophages, smooth muscle cells and endothelial cells) and activated platelets.

The detection via the PMBC or the PMBC-Conjugate may also take place for the purposes of basic research, in the study of apoptosis in tissue culture or in animal models.

In accordance with another approach of the invention, the present invention concerns a pharmaceutical composition comprising a PMBC or a PMBC-Conjugate as an active ingredient, optionally with a pharmaceutically acceptable carrier; the PMBC or the PMBC-Conjugate comprises (i) a medicinally-useful, pharmaceutically-active drug; and (ii) a PMBC. The PMBC or the PMBC-Conjugate may act to target the drug to PNOM-cells, and can therefore be useful for the treatment of a disease characterized by the presence of PNOM-cells as defined above.

By the term "pharmaceutically acceptable" it is included that the formulation is sterile and pyrogen-free. Suitable pharmaceutical carriers are well known in the art of pharmacy. The carrier(s) must be "acceptable" in the sense of being compatible with the compound of the invention and not deleterious to the recipients thereof. Typically, the carriers will be water or saline which will be sterile and pyrogen free; however, other acceptable carriers may be used.

The pharmaceutical composition which comprises the PMBC or the PMBC-Conjugate of the invention may be administered by any of the known routes, inter alia, oral, intravenous, intraperitoneal, intramuscular, subcutaneous, sublingual, intraocular, intranasal or topical administration. The carrier should be selected in accordance with the desired mode of administration, and include any known components, e.g. solvents; emulgators, excipients, etc. The pharmaceutical composition may comprise, if desired, also other pharmaceutically-active compounds which are used to treat the disease, eliminate side effects or augment the activity of the active component.

Typically the pharmaceutical compositions or formulations of the invention are for parenteral administration, more particularly for intravenous administration. Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulation of drugs is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

Injectable preparations, for example, sterile injectable aqueous or oleaginous suspensions, can be formulated according to the known art using suitable dispersing or wetting agents and suspending agents. The sterile injectable preparation may also be a sterile injectable solution or suspension in a nontoxic parenterally acceptable diluent or solvent. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and non-ionic detergents, and polyethylene glycols can also be used. Mixtures of solvents and wetting agents such as those discussed above are also useful.

The amount of active ingredient that can be combined with the carrier materials to produce a single dosage form will vary depending upon the patient and the particular mode of administration.

The association between the medicinally-useful drug and the PMBC may be either by covalent binding, by non-covalent binding (e.g., electrostatic forces) or by formation of carrier particles (such as liposomes) comprising the drug and having on their surface a PMBC, which targets the complex to the PNOM cells.

The purpose of a PMBC or PMBC-Conjugate, which are linked to drug which exert therapeutic effect, is to selectively bind to PNOM-cells and to tissues and organs comprising these cells in diseases or disorders such as those specified above. Once the drug reaches the target it will exert its physiological activity, either when still being in complex as part of the PMBC-Conjugate, or after disconnecting from the PMBC unit (for example by cleavage, destruction, activity of natural enzymes, etc.) by any other known mechanism.

The drug, or as is also termed here the "pharmaceutically active substance", should be chosen in accordance with the specific disease for which the composition is intended.

Accordingly, the invention provides a method of delivering a pharmaceutically active substance to a cell, comprising the step of contacting the cell with an effective amount of a PMBC-Conjugate which comprises a PMBC, a pharmaceutically active substance, and a linker moiety linking the PMBC and the pharmaceutically active substance.

In another aspect, the present invention provides a method for improving the treatment, inhibition or prevention of a medical disorder; by creating a PMBC-Conjugate, comprising a PMBC and a pharmaceutically active substance, known to be useful for treating, inhibiting, or preventing the disease. The improvement of treatment, inhibition or prevention can thus be achieved, by the selective targeting of the Conjugate to the foci of disease, via targeting to the PNOM-cells comprised within the foci. Examples for such medical disorders are described above.

In another embodiment of the invention, there is provided a method for targeting an anticoagulant or a fibrinolytic agent to a blood clot, comprising the step of administering a PMBC-Conjugate according to the invention, comprising an anticoagulant or a fibrinolytic agent, thereby achieving targeting of the therapeutic agent to the blood clot.

The PMBC or PMBC-Conjugate may be used for the treatment, amelioration or prevention of diseases which are manifested by initiation or propagation of abnormal and excessive blood clotting, diseases manifested by inappropriate and excessive apoptosis such as degenerative disorders, neurodegenerative disorders, inflammatory disorders, and/or diseases associated with immune-mediated etiology or pathogenesis, such as auto-immune disorders. These medical disorders may be without limitation any of the diseases mentioned above.

For the treatment or prevention of unstable atherosclerotic plaque, characterized by thrombosis or apoptosis, the drug can be chosen from the above groups of drugs.

In another embodiment of the invention, there is provided a method of targeting anticancer drugs to a tumor which has foci of apoptotic cells, the method comprising the step of administering a PMBC-Conjugate according to the invention, comprising a cytotoxic drug, thereby achieving targeting of the drug to the foci of cell death within the tumor.

The PMBC-Conjugate of the invention, comprising an anticancer drug may be used to enhance the efficacy of anticancer protocols. The enhancement of an anti-cancer protocol is achieved by either: (1). Targeting of the Conjugate to the tumor tissue; such tissue is often characterized by an abnormally excessive apoptotic load (the latter often being correlated to the level of tumor aggressiveness); (2). Use of two waves of apoptosis: the first wave being achieved by using a standard chemotherapeutic or radiotherapeutic agent, aimed at initiating an apoptotic process within the tumor; followed by a second wave of apoptosis, in which the anticancer drug is administered as part of a PMBC-Conjugate, thus being targeted to the apoptotic cells produced by the first wave. Thus, selective augmentation of the local concentrations of the anticancer drug within the tumor mass is achieved, with consequent enhancement of the local tumor-killing process, while maintaining relatively lower levels of the drug in non-tumor tissues.

In accordance with this aspect, the present invention still further concerns a method for improvement of treatment of a disease manifested by PNOM-cells, by improving the targeting of a drug useful for the treatment of the disease to the foci of the disease in the body of the individual. The method comprises administering to the individual in need of such treatment an effective amount of a PMBC or a PMBC-Conjugate, comprising a drug known to be useful for the treatment of the disease of the individual. The PMBC-Conjugate allows for the selective targeting of the active drug to the tissues inflicted by the disease. The tissues comprise PNOM-cells, and thus the method of the invention acts to augment the local concentrations of the active drug in the diseased tissue, and to enhance the therapeutic effect of the drug at the target site.

The term "effective amount" refers to an amount capable of decreasing, to a measurable effect, at least one adverse manifestation of the disease. It should be chosen in accordance with the drug used, the mode of administration, the age and weight of the patient, the severity of the disease, etc.

By another approach of the invention, the properties of the PMBCs to bind specifically to PNOM-cells are utilized to clear body fluid of the cells. The body fluid may be in one embodiment blood or a blood product.

According to this embodiment, the invention provides a PMBC immobilized on a solid support. The immobilization may be by direct attachment, either by covalent or non-covalent binding, or by attachment through a spacer. The immobilized PMBC is intended to clear a body fluid from PNOM-cells.

The term "solid support" refers in the contents of the present invention to a solid matrix, an insoluble matrix, and an insoluble support. The solid support in accordance with the present invention may be formed in a variety of structures such as a stack of micro-particulates, micro-filters, or micro-capillara, and may be composed of various materials such as alumina, diatomaceous earth, celite, calcium carbonate, calcium sulfate, ion-exchange resin, silica gel, charcoal, amberlite, dowex, Eupergit and ethylsofoxycellulose.

The compounds immobilized on a solid support form part of a filter device. Thus in accordance with the clearance approach, the present invention her concerns a filter device comprising a housing containing the PMBC immobilized on the solid support, and a fluid inlet and fluid outlet. Body fluids such as blood or blood products enter the housing through the inlet, come into contact and adhere to the immobilized PMBC contained in the housing. Thus, the body fluid is cleared of circulating cells having perturbed membranes, such as damaged or dying cells, or cleared of larger structures such as emboli having PNOM-membranes Consequently, fluid exiting from the outlet has a reduced content of the PNOM-cells or is essentially devoid of same.

EXAMPLES

In order to understand the invention and to see how it may be carried-out in practice, some embodiments will now be described, in which detection of binding of the compounds of the present invention to cells undergoing PNOM due to apoptosis was evaluated.

The performance of several compounds, all having the general structure of formula I will be demonstrated, thus showing the role of the structural features of formula I in determining the performance of the PMBC of the invention in selective binding to PNOM-cells.

Performance of the compounds in selective binding to PNOM-cells was measured both in vitro in tissue culture studies, by monitoring of the intrinsic fluorescence of the compounds using flow cytometric (FACS) analysis; and following intravenous administration of the compounds in vivo, by detection of the intrinsic fluorescence via fluorescent microscopy of tissue sections. These embodiments will now be described by way of non-limiting example only, with reference to the accompanying drawings.

Example 1

Synthesis of (5-Butylmethylamino-naphtalene-1-sulfonyl)-glycine (NST703)

a. 5-Butylamino-naphthalene-1-sulfonic acid (1)

A mixture of 1-amino-naphthalene-1-sulfonic acid (111 g, 0.497 mol), sodium hydrogen carbonate (124 g, 1.48 mol) and 1-bromobutane (79 mL, 0.734 mol) in dimethyl formamide (2.2 L) was stirred and heated to 125° C. for 2.5 hours. The mixture was poured into a mixture of water (13 L) and sodium chloride (2.90 kg), and pH was lowered from 8.9 to 3.0 with concentrated hydrochloric acid, and the solid, which formed, was isolated by filtration, washed with water (3 times 250 mL), and dried giving 53.9 g of a brown powder. The solid was dissolved in water (2.5 L) by adding sodium hydrogen carbonate (22.4 g, 0.267 mol). Hydrochloric acid (3 M, 78 mL) was added in order to lower the pH from 7.9 to 3.0. Precipitate was isolated by filtration, and dried in at 50° C., giving 47.9 g of a brown solid. Recrystallization (isopropanol water 2:1) gave 44.5 g of 1 (32%).

b. 5-Butylmethylamino-naphthalene-1-sulfonic acid (2)

1 (42.7 g, 0.153 mol) was suspended in water (850 mL), and sodium hydrogen carbonate (38.6 g, 0.459 mol) was added. The resulting solution was stirred at 15° C. and dimethyl sulfate (15 mL, 0.16 mol) was added. After 6 hrs., more dimethyl-sulfate (15 mL, 0.16 mol) was added. The solution was stirred overnight, heated to 80° C. for 0.5 hour. After cooling to room temperature, the pH was adjusted to 3.0. The solid, which formed overnight, was filtered, washed with water and dried at 50° C., giving 32.8 g (73%) of a brown powder 2.

c. 5-Butylmethylamino-naphthalene-1-sulfonyl chloride (3)

2 (23.9 g, 0.081 mol) was cooled with ice under nitrogen and mixed with phosphorus pentachloride (18.7 g, 0.0896 mol). The mixture was heated on a water bath at 60° C. for 2 hours and poured into a mixture of ice (164 g) and water (341 g). Ethyl acetate (400 mL) and sodium hydrogen carbonate (50 g, 0.60 mol) were added. The phases were separated and the water phase was extracted with ethyl acetate. The combined organic phases were washed, dried (sodium sulphate), and treated with activated carbon (1.1 g). Evaporation of the solvent gave 20.8 g of 3 as an oil. The product can be purified by chromatography.

d. 5-Butylmethylamino-naphthalene-1-sulfonyl)-glycine (NST703)

Two mmoles of L-glycine and 3 mmoles of $NaHCO_3$ were dissolved in 5 ml of water. A solution containing 1 mmol of 3 in acetone was slowly added. More acetone was added until the solution was clear. The mixture was stirred overnight at room temperature, and protected from light. Acetone was removed by flash evaporation and the remaining water solution was acidified to pH=4.5 to 5 by adding 2M citric acid. Then, NaCl was added until saturation and the solution was extracted with three portions of ethyl acetate (20 ml each). The extracts were combined, dried over $MgSO_4$ and the solution filtered Solvent was removed and residue purified by liquid chromatography on silica gel. A gradient of 0 to 5% methanol in dichloromethane was used as eluent. Fractions containing desired products were combined and solvents removed. The residue was triturated in 1:1 ether: petroleum ether. Precipitate was filtered out and dried in vacuum overnight thus affording 5-Butylmethylamino-naphtalene-1-sulfonyl-glycine (NST703).

The NMR data were as follows:
$^1$H-NMR ($CDCl_3$, δ=ppm): 8.58 (1H, d); 8.33 (1H, d); 8.22 (1H, d); 7.53 (2H, m); 7.26 (1H, m); 3.71 (2H, s); 3.10 (2H, t); 2.88 (3H, s); 1.66 (2H, m); 1.32 (2H, m); 0.87 (3H, t). ESI-MS: Consistent. m/z+H$^+$=351.7.

Example 2

Synthesis of (5-dibutylamino-naphthalene-1-sulfonyl)-L-aspartic acid (NST705)

Two mmoles of aspartic acid and 4 mmoles of $NaHCO_3$ were dissolved in 5 ml of water. A solution containing 1 mmol of 5-dibutylamino-naphthalene-1-sulfonyl chloride (Bansyl chloride, Purchased from TCI) in acetone was slowly added. More acetone was added until the solution was clear. The mixture was stirred overnight at room temperature and protected from light. Acetone was removed by flash evaporation and the remaining water solution was acidified to a of pH=4.5 to 5 by adding 2M citric acid. Then, NaCl was added until saturation and the solution was extracted with three portions of ethyl acetate (20 ml each). Extracts were combined, dried over $MgSO_4$ and the solution was filtered. The solvent was removed and the residue was purified by liquid chromatography on a silica gel. A gradient of 0 to 5% methanol in dichloromethane was used as eluent. Fractions containing the desired product were combined and solvents removed. The residue was triturated in 1:1 ether: petroleum ether. The precipitate was filtered out and dried in vacuum overnight thus affording 5-dibutylamino-naphthalene-1-sulfonyl)-L-aspartic acid (NST705).

$^1$H-NMR ($CD_3OD$, δ=ppm): 8.63 (1H, d); 8.38 (1H, d); 8.27 (1H, d); 7.55 (2H, m); 7.34 (1H, d); 3.84 (1H, broad); 3.11 (1H, d); 8.63 (4H, t); 2.68 (2H, broad); 1.43 (4H, m); 1.30 (4H, m); 0.85 (6H, t). ESI-MS: Consistent. m/z+H$^+$=451.4.

Example 3

Selective Binding of NST705 to Apoptotic Jurkat Cells; Flow-cytometric (FACS) Analysis Cultured Jurkat cells (human adult T cell leukemia cells) were grown in suspension in RPMI medium (Beit-Haemek, Israel), supplemented with 10% of fetal calf serum (FCS), 4 mM of L-glutamine, 1 mM of sodium pyruvate, 1 nM $CaCl_2$ and antibiotics (100 units/ml penicillin; 100 μg/ml streptomycin and 12.5 units/ml of nystatin). Prior to induction of apoptosis, medium was replaced with HBS buffer (10 mM HEPES; 140 mM NaCl, 1 mM CaCl). Apoptosis was then triggered by treatment with anti-Fas Ab (0.1 μg/ml; 3 hrs). As a result, a marked percentage of the cells became apoptotic, and is regarded as newly formed early apoptotic cells. Non-treated cells served as control. Both control cells and apoptotic cells were then incubated for 20 minutes with 100 μM of NST705. Subsequently, cells were co-stained with propidium iodide (PI), a marker of membrane disintegration during late phases of cell death, and the selective binding of the NST705 compounds to control and apoptotic cells was determined by flow cytometric (FACS) analysis using Becton-Dickinson cell sorter and CellQuest software (excitation was at 356 nm and emission was measured at 530 nm). The analysis shown in FIG. 1 describes the uptake of NST705 compound into the population of apoptotic cells in control and anti-fas treated cultures.

In the dot plot shown in FIG. 1A and FIG. 1B, the left lower quadrant represents the healthy, non-stained fraction of cells. The right lower quadrant represents the newly formed population of cells in the early stages of apoptosis. These cells still maintain membrane integrity and thus exclude PI. Cells binding both NST705 and PI, i.e., cells in the late stages of apoptosis are represented in the right upper quadrant.

Figure 1C:
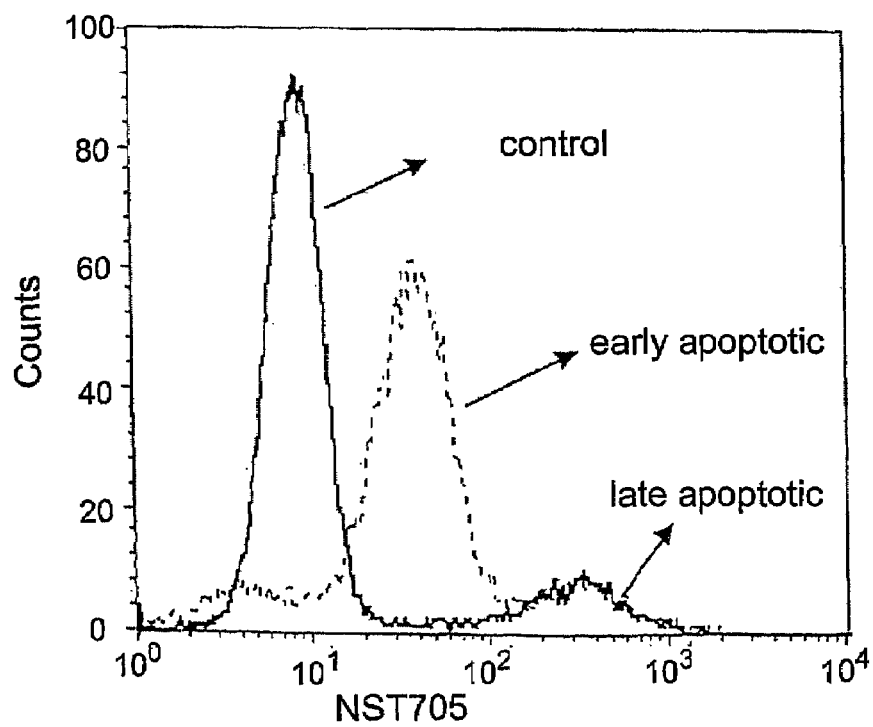
FIG. 1C is a histogram analysis of the data presented in FIGS. 1A and 1B.

The induction of apoptosis was associated with the emergence of a marked, distinct population of cells in the early, stages of the apoptotic process, selectively binding NST705 and occupying the right lower quadrant of the plot. The percent of identified early apoptotic events within the population is 70.8% in the apoptotic cells as compared with 3% of the non-treated control cells. FIG. 1C is a histogram analysis of the data presented in FIG. 1A and 1B. The emergence of a new and distinct peak of highly fluorescent cells in the early phase of the apoptotic process is clearly associated with anti-Fas treatment.

Example 4

Selective Binding of NST703 to Apoptotic Jurkat Cells; Flow-cytometric (FACS) Analysis Cultured Jurkat cells (human adult T cell leukemia cells) were grown in suspension in RPMI medium (Beit-Haemek, Israel), supplemented with 10% of fetal calf serum (FCS), 2 mM of L-glutamine, 1 mM of sodium pyruvate, 1 mM 1 mM HEPES and antibiotics (100 units/ml penicillin; 100 µg/ml streptomycin and 12.5 units/ml of nystatin). Prior to induction of apoptosis, medium was replaced with HBS buffer (10 mM HEPES; 140 mM NaCl, 1 mM CaCl). Apoptosis was then triggered by treatment with anti-Fas Ab (0.1 µg/ml; 3 hrs). As a result, a marked percentage of the cells became apoptotic. Non-treated cells served as control. Both control cells and apoptotic cells were then incubated for 20 minutes with 100 µM of NST703. Subsequently, cells were co-stained with propidium iodide (P). Binding of NST703 to the control and apoptotic cells was determined by flow cytometric (FACS) analysis using Becton-Dickinson cell sorter and CellQuest software (excitation was at 356 nm and emission was measured at 530 nm). The analysis is shown in FIG. 2.

In the dot plot shown in FIG. 2A and 2B, the left lower quadrant represents the healthy, non-stained fraction of cells. The right lower quadrant represents the newly formed population of cells in the early stages of apoptosis. These cells still maintain membrane integrity and thus exclude PI. Cells binding both NST703 and PI, i.e., cells in the late stages of apoptosis are represented in the right upper quadrant.

The induction of apoptosis was associated with the emergence of a marked, distinct population of cells in the early stages of the apoptotic process, selectively binding NST703 and occupying the right lower quadrant of the plot. The percent of identified early apoptotic events within the population is 75.6% in the apoptotic cells as compared with 3.27% of the non-treated control cells. FIG. 2C is a histogram analysis of the data presented in FIG. 2A and FIG. 2B. The emergence of a new and distinct peak of highly fluorescent cells in the early phase of the apoptotic process is clearly associated with anti-Fas treatment.

Example 5

In-Vivo Targeting of NST705 to Chemotherapy-induced Apoptotic Cells of Lymphoma Tumors in Mice Lymphoma tumors were induced in 8 weeks old male DBA/2 mice (Harlan laboratories, UK) by subcutaneous injection of lymphoma cells.

The cells, from a chemically-induced LY-R clone were obtained from ATCC(CRL-1722), and maintained by subsequent passages in mice. For induction of tumors, $5 \times 10^5$ cells in a volume of 100 µl were injected into the thigh region in mice. After 10 days, when tumor diameter reached the size of 5-7 mm, mice were subjected to chemotherapy treatment (Taxol, 20 mg/Kg, intra-peritoneal injection). Twenty-four hours later, NST705 was injected systemically at a dose of 1.4 mg/mouse. Two hours later, mice were sacrificed and tumors were frozen in liquid nitrogen. Cryosections were then prepared and serial slides were subjected to either hematoxylin & eosin (H&E) staining or fluorescent microscopy evaluation (excitation wavelength of 360 nM, emission at 530 nm), using an Olympus fluorescent microscope (model IX70).

As shown in FIG. 3A, cells undergoing cell death can be identified in the H&E staining by the chromatin condensation and the strongly-eosinophilic cytoplasm. These cells also manifested marked uptake of NST705 (FIG. 3B). Indeed, a large number of such cells undergoing a death process and manifesting marked uptake of NST705 are demonstrated. By contrast, such uptake was not observed in the viable, non-apoptotic tumor cells, which remained dark. These findings therefore demonstrate the selective targeting of NST705 to cells undergoing cell death in tumor tissue.

Example 6

Selective Binding of DC to Apoptotic Jurkat Cells; Flow-cytometric (FACS) Analysis Cultured Jurkat cells (human adult T cell leukemia cells) were grown in suspension in RPMI medium (Beit-Haemek, Israel), supplemented with 10% of fetal calf serum (FCS), 2 mM of L-glutamine, 1 mM of sodium pyruvate, 1 mM 1 mM HEPES and antibiotics (100 units/ml penicilin; 100 µg/ml streptomycin and 12.5 units/ml of nystatin). Prior to induction of apoptosis, medium was replaced with HBS buffer (10 mM HEPES; 140 mM NaCl, 1 mM CaCl). Apoptosis was then triggered by treatment with anti-Fas Ab (0.1 µg/ml; 3 hrs). As a result, a marked percentage of the cells became apoptotic. Non-treated cells served as control. Both control cells and apoptotic cells were then incubated for 20 minutes with 100 µM of DC. Subsequently, cells were co-stained with propidium iodide (PI). Binding of DC to the control and apoptotic cells was determined by flow cytometric (FACS) analysis using Becton-Dickinson cell sorter and CellQuest software (excitation was at 356 nm and emission was measured at 530 nm). The analysis is shown in FIG. 4.

FIG. 4A and FIG. 4B are each a representative FACS dot plot, showing that activation of apoptosis leads to a marked uptake of DC by cells in the early stages of apoptosis (FIG. 4B), as compared to control cells (FIG. 4A). The UV-axis denotes fluorescence intensity of DC; $FL_2$-axis denotes fluorescence intensity of propidium iodide (PI).

In control non-treated cells (FIG. 4A), only a minor percentage of the cells are in the early apoptotic stage (2.3%, right lower quadrant). However, upon induction of apoptosis (FIG. 4B), there is an emergence of a large population (76%) of cells in the early stages of apoptosis, manifesting a marked uptake of DC, yet maintaining membrane integrity (i.e., do not bind PI; right lower quadrant).

FIG. 4C is a flow-cytometric (FACS) histogram representation of the data shown in FIG. 4A and 4B. The x-axis denotes fluorescence intensity of DC, while the counts axis denotes the percentage of events. Control cells are marked by a solid line, while anti-Fas-Ab-treated cells are marked by a dotted line. Treatment with the anti-Fas antibody results in a marked shift in the UV fluorescence of cells, reflecting their acquisition of the feature of a marked uptake of DC in the early stage of the apoptotic death process.

Example 7

Targeting of DC In-Vivo to Apoptotic Cells in Tumor, Murine Melanoma

Tumors, and especially aggressive malignancies such as melanoma are characterized, in addition to the abnormal tissue proliferation, also by marked apoptosis of tumor cells. The performance of DC in selective targeting of these apoptotic cells within the tumor was therefore examined Mice (c57/black; 8 weeks old male mice) were injected subcutaneously bilaterally, in the flank, with murine melanoma-derived B16-F10 cells (ATCC CRL-6475; $10^5$ cells/mice in a volume of 100 µl). Prior to injection, the cell line was maintained in culture in Dulbecco's modified Eagle's medium (DMEM), supplemented with 4 mM of L-glutamine; 100 units/ml of penicillin; 100 µg/ml of streptomycin; 12.5 units/ml of nystatin and 10% of fetal calf serum (FCS). Tumors were allowed to grow for 14 days, by which they reached a diameter of 5-7 mm.

The DC compound (2 mg/mouse in NaPpi buffer, pH. 7.40) was injected intravenously. Two hours later, the mice were scarified and the tumors, as well as other organs were taken, and immediately frozen in liquid nitrogen. Frozen sections were then prepared from each of the organs. Uptake of DC by the tumors or other organs was assessed by fluorescent microscopy.

Figure 5A:
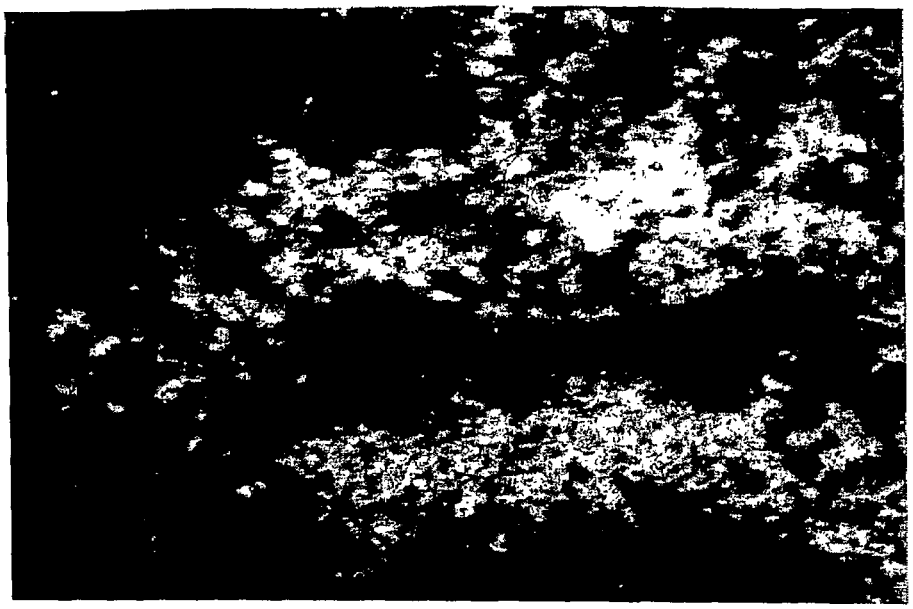
FIG. 5A shows fluorescent microscopy of the tumor. Extensive binding of DC to numerous tumor cells undergoing apoptosis can be observed.

FIG. 5A shows fluorescent microscopy of the tumor. Extensive binding of DC to numerous tumor cells undergoing apoptosis can be observed. Demonstrated are also the intracellular accumulation of the compound, and the high level of selectivity, reflected by a marked uptake into the apoptotic cells, while viable tumor cells remain unstained.

Figure 5B:
FIG. 5B shows fluorescent microscopy of small intestine tissue of the same animal, showing lack of binding of the compound to the normal, viable tissue.

This high level of selectivity is also demonstrated in FIG. 5B, showing fluorescent microscopy of small intestine tissue of the same animal, showing lack of binding of the compound to the normal, viable tissue. Similar results were obtained from various other non-target tissues, such as colon, kidney, spleen, muscle and heart.

Example 8

The Terminal Dansyaltion Labeling Method (TDLM)

The short half-life (about 110 minutes) of $^{18}F$ dictates specific conditions for the attachment of this isotope as a marker of the PMBC of the invention for PET imaging. The conditions include, among others, rapid reactions in basic solutions and relatively high temperatures (the "PET Hot Box chemistry"). These conditions may not be compatible with the relatively sensitive sulfonamide subunit of the PMBC of the invention. Undesirable side reactions may also occur. In order to overcome these potential difficulties, the terminal dansylation labeling method was developed (TDLM). According to the method, the PMBC is regarded as comprising two subunits: the amine subunit, to which the $^{18}F$ should be linked, and the sulfonic acid subunit, e.g., dansyl. According to the method, $^{18}F$ is being first attached to the amine subunit. Only as a terminal step before purification, the sulfonic acid subunit is being attached to the fluorinated amine subunit, thus forming the desired compound. Optimization of this reaction conditions allows now the performance of the terminal step of dansylation in 10 minutes, thus rendering the synthesis compatible with the timeframe of the $^{18}F$ attachment in the "PET hot box" scenario.

In order to demonstrate the methodology of fluorine attachment to the compounds of the invention and the terminal dansylation labeling method, the synthetic scheme of NST730, comprising $^{19}F$ is described. The compound was synthesized by Albany Molecular Research Inc. (Albany, N.Y., USA), according to the following synthetic scheme:

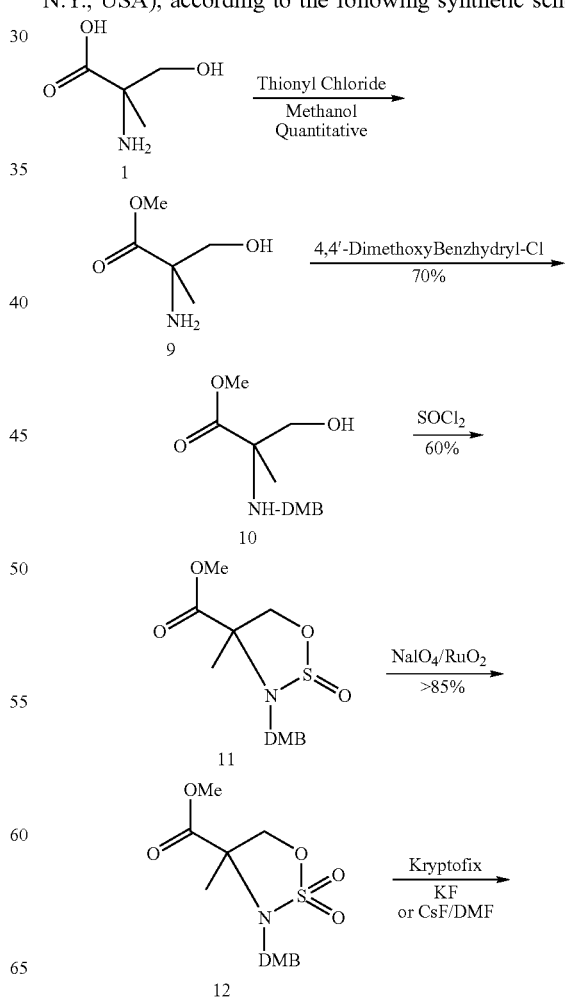

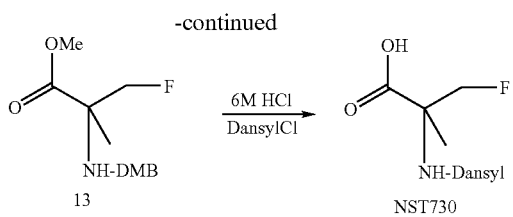

Example 9

Targeting of NST730 in-vivo to Apoptotic Cells in Tumor, Murine Melanoma

The performance of NST730 in selective targeting to apoptotic cells within a tumor examined as described in Example 7. Mice (c57/black; 8 weeks old male mice) were injected subcutaneously bilaterally, in the flank, with murine melanoma-derived B16-F10 cells (ATCC CRL-6475; $10^5$ cells/mice in a volume of 100 µl). Tumors were allowed to grow for 14 days, by which they reached a diameter of 5-7 mm.

The NST730 compound (2 mg/mouse in NaPpi buffer, pH. 7.40) was injected intravenously. Two hours later, the mice were scarified and the tumors, as well as other organs were taken, and immediately frozen in liquid nitrogen. Frozen sections were then prepared from each of the organs. Uptake of NST730 by the tumors or by other organs was assessed by fluorescent microscopy.

Figure 6A:
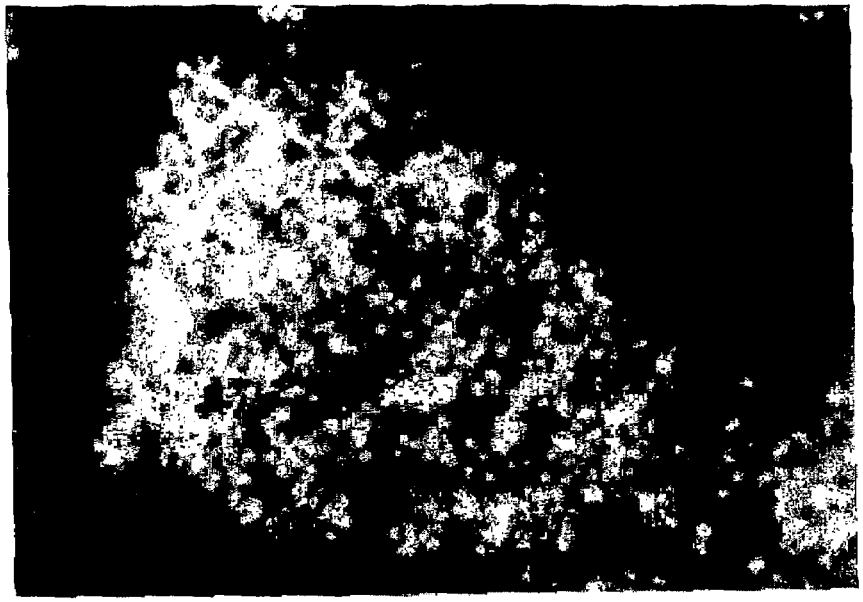
FIG. 6A shows fluorescent microscopy of the tumor. Extensive binding of NST730 to numerous tumor cells undergoing apoptosis can be observed.

FIG. 6A shows fluorescent microscopy of the tumor. Extensive binding of NST730 to numerous tumor cells undergoing apoptosis can be observed. Demonstrated are also the intracellular accumulation of the compound, and the high level of selectivity, reflected by a marked uptake into the apoptotic cells, while viable tumor cells remain unstained.

Figure 6B:
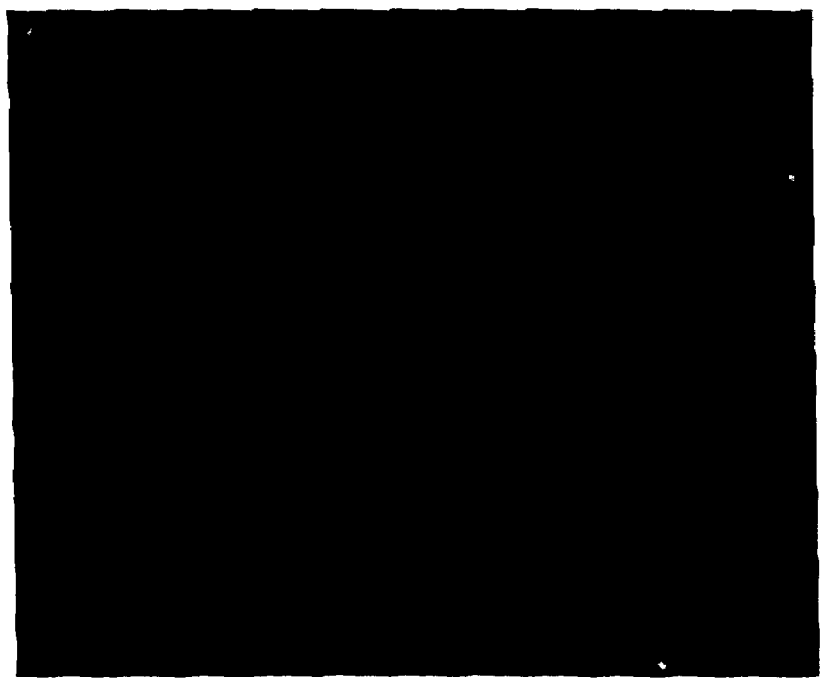
FIG. 6B shows fluorescent microscopy of muscle tissue of the same animal, showing lack of binding of the compound to the normal, viable tissue.

This high level of selectivity is also demonstrated in FIG. 6B, showing fluorescent microscopy of muscle tissue of the same animal, showing lack of binding of the compound to the normal, viable tissue. Similar results of lack of significant binding were obtained from various other non-target tissues, such as colon, kidney, spleen and heart.

Example 10

Detection by NST732 of Cell Death Induced by Irradiation in vivo; Murine Lymphoma DBA mice (5-6 weeks old males, Jackson laboratories) were injected subcutaneous with $10^6$ lyS cells in 50 µl saline and were examined daily for tumor formation. At days 8, 9 and 10 mice were placed in a Perspex box and irradiated with 6MV x-rays apparatus (Linac) in fractions of 6 Gray each. Each mouse received a dose of about 1.0 centiGray per monitor unit. At day 13 (72 hours following the last irradiation) mice were injected intravenously with NST 732 (70 mg/kg, dissolved in Tris base containing 25% cremophore RH410, pH=9). After 2 hours, tumors were excised, frozen in liquid nitrogen and submitted for histopathological assessment.

Figure 7A:
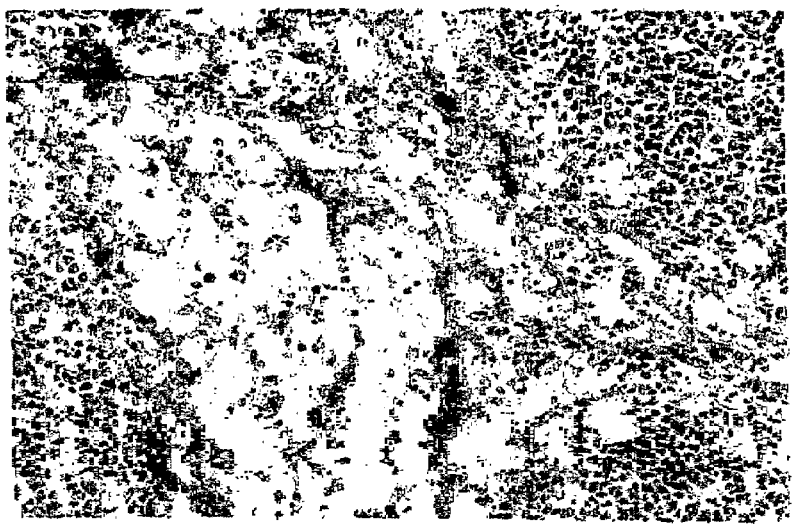
FIG. 7 (A-C): Selective binding of NST732 to murine lymphoma cells undergoing cell death induced by irradiation in vivo: 7A: H&E staining 7B: binding of NST732; fluorescent microscopy; 7C: TUNEL staining.
Figure 7B:
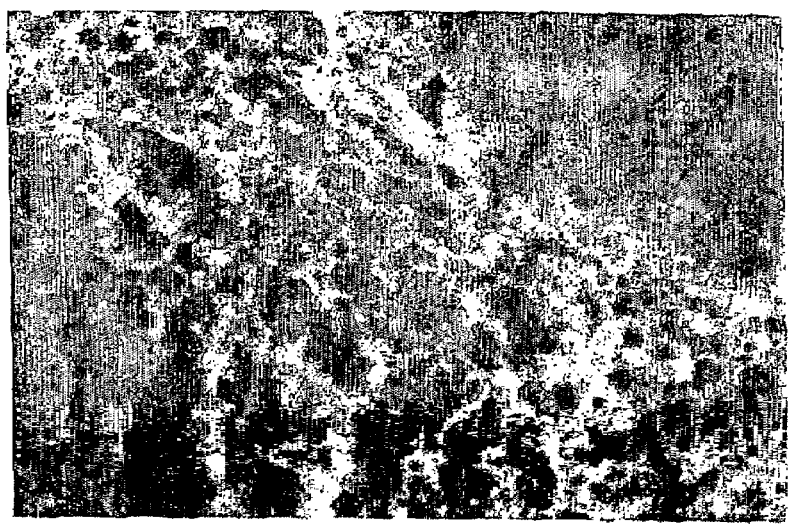
Figure 7C:
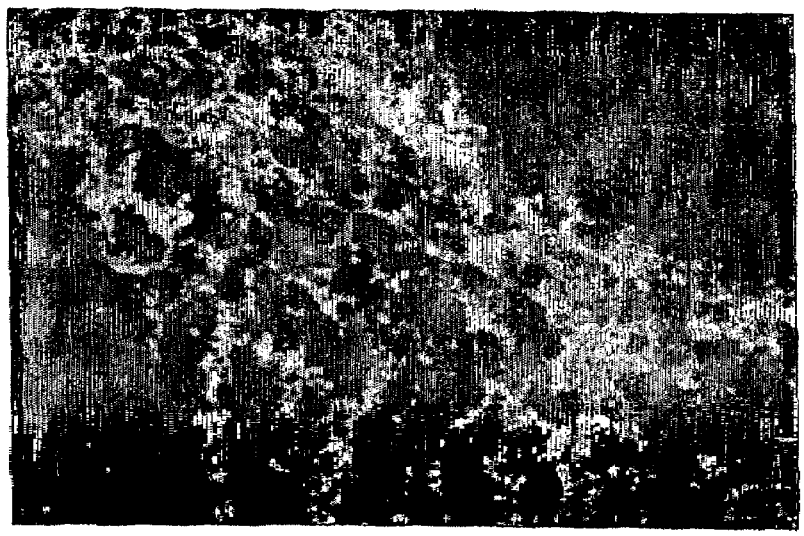
Figure 8A:
FIG. 8 (A-D): Detection of cell death by NST 732, following middle cerebral artery (MCA) occlusion; computerized fluorescent imaging.
Figure 8B:
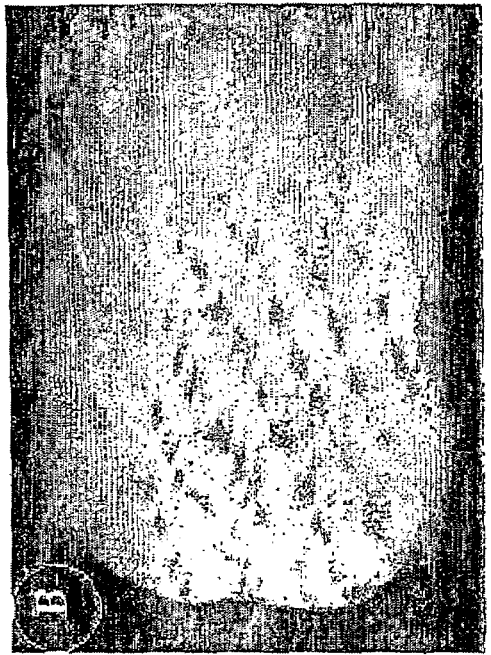
Figure 8C:
Figure 8D:
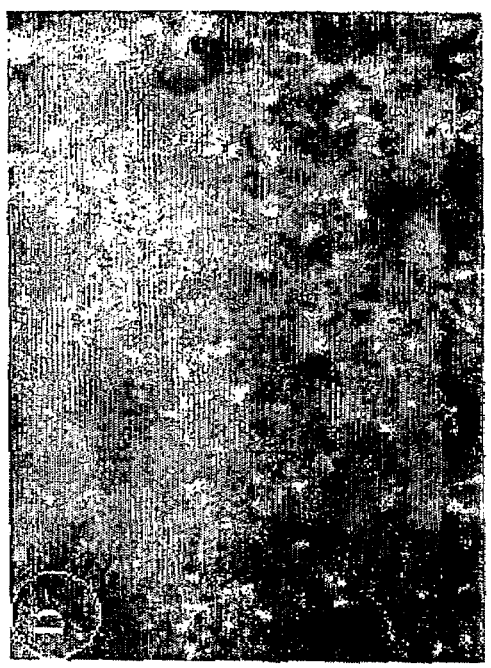

As shown in FIG. 7B, showing fluorescent microscopy of the tumor, extensive binding of NST732 to numerous tumor cells undergoing apoptosis can be observed. The identity of the cells manifesting uptake of NST732 as cells undergoing cell death was confirmed by H&E and TUNEL staining, performed on consecutive slides (FIGS. 7A and 7C, respectively).

This Example therefore shows the ability of NST732 to bind to tumor cells undergoing cell death induced by irradiation, a common mode of anti-cancer treatment used in clinical practice, thus showing the important potential of this compound in imaging the effect of this mode of therapy.

Example 11

Detection of Neuronal Cell Death, Following Middle Cerebral Artery (MCA) Occlusion by NST 732

Cerebral ischemia was induced in Balb/C mice (10-12 weeks) by cauterization of the middle cerebral artery. Mice were anesthetized, and the temporal bone was exposed. Scraping off the bone up to a minimal hole allowed exposure of the artery subjecting it to cauterization. 22 hours later, NST732 (70 mg/kg) was injected intravenously. Two hours later (at 24 h from induction of the injury), mice were anesthetized and sacrificed, and brains were removed into liquid nitrogen for histopathological analysis of the frozen sections. Four µm thick sections were prepared for fluorescent microscopic analysis to follow the cells stained positively with NST732.

As can be clearly seen from FIGS. 8A-D, cells in the infracted area manifested extensive binding of NST 732. By contrast, cells outside the infracted area did not manifest significant binding of the compound.

These results therefore manifest the ability of NST732 to image neuronal cell death in vivo, and can therefore be a useful tool for the diagnosis and follow-up of cerebral stroke.

Example 12

Detection of Neuronal Cell Death, Following Middle Cerebral Artery (MCA) Occlusion by NST 730

Cerebral ischemia was induced in Balb/C mice (10-12 weeks) by cauterization of the middle cerebral artery. Mice were anesthetized, and the temporal bone was exposed. Scraping off the bone up to a minimal hole allowed exposure of the artery subjecting it to cauterization, 22 hours later, NST730 (70 mg/kg) was injected intravenously. Two hours later (at 24 h from induction of the injury), mice were anesthetized and sacrificed, and brains were removed into liquid nitrogen for histopathological analysis of the frozen sections, as described in Example 11.

Figure 9B:
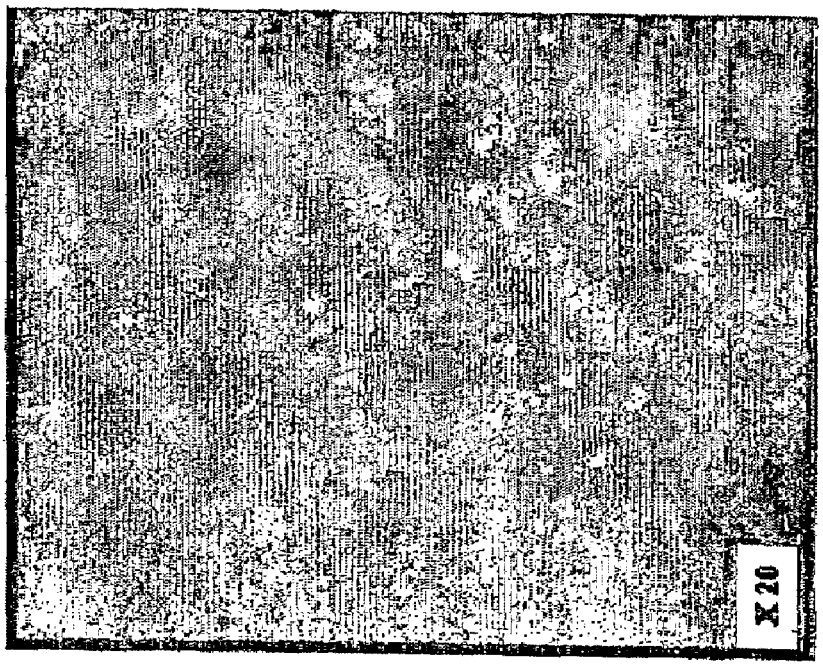
FIG. 9 (A-B): Detection of cell death by NST 730, following middle cerebral artery (MCA) occlusion.
Figure 9A:

As can be clearly seen from FIG. 9, cells in the damaged area showed extensive binding of NST 730 (FIG. 9A). By contrast, cells outside the infracted area did not manifest significant binding of the compound (FIG. 9B).

These results therefore manifest the ability of NST730 to image neuronal cell death in vivo, and can therefore be a useful tool for the diagnosis and follow-up of cerebral stroke.

Example 13

Synthesis of 5-Butylmethylamino-naphtalene-1-sulfonic acid (NST601)

a. 5-Butylamino-naphthalene-1-sulfonic acid (1)

A mixture of 5-amino-naphthalene-1-sulfonic acid (111 g, 0.497 mol), sodium hydrogen carbonate (124 g, 1.48 mol) and 1-bromobutane (79 mL, 0.734 mol) in dimethyl formamide (2.2 L) was stirred and heated to 125° C. for 2.5 hours. The mixture was poured into a mixture of water (13 L) and sodium chloride (2.90 kg), and pH was lowered from 8.9 to 3.0 with concentrated hydrochloric acid, and the solid, which formed, was isolated by filtration, washed with water (3 times 250 mL), and dried giving 53.9 g of a brown powder. The solid was dissolved in water (2.5 L) by adding sodium hydrogen carbonate (22.4 g, 0.267 mol). Hydrochloric acid (3 M, 78 mL) was added in order to lower the pH from 7.9 to 3.0. Precipitate was isolated by filtration, and dried in at 50° C., giving 47.9 g of a brown solid. Recrystallization (iso propanol water 2:1) gave 44.5 g of 1 (32%).

b. 5-Butylmethylamino-naphthalene-1-sulfonic acid (2)

Compound 1 (42.7 g, 0.153 mol) was suspended in water (850 mL), and sodium hydrogen carbonate (38.6 g, 0.459 mol) was added. The resulting solution was stirred at 15° C. and dimethyl sulfate (15 mL, 0.16 mol) was added. After 6 hrs., more dimethylsulfate (15 mL, 0.16 mol) was added. The solution was stirred overnight, heated to 80° C. for 0.5 hour. After cooling to room temperature, the pH was adjusted to 3.0. The solid, which formed overnight, was filtered, washed with water and dried at 50° C., giving 32.8 g (73%) of a brown powder 2.

Example 14

Synthetic Route to 5-hydroxypropyl-methyl-amino-naphthalene-1-sulfonic acid (NST602), and 5-fluoropropyl-methyl-amino-naphthalene-1-sulfonic acid (NST603)

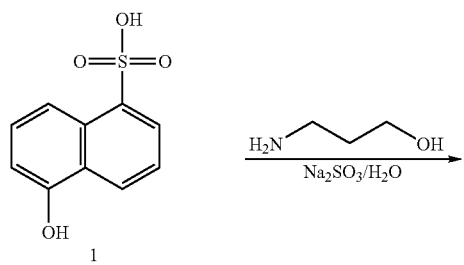

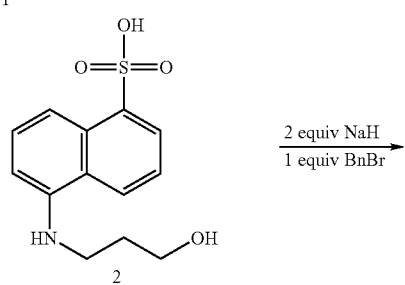

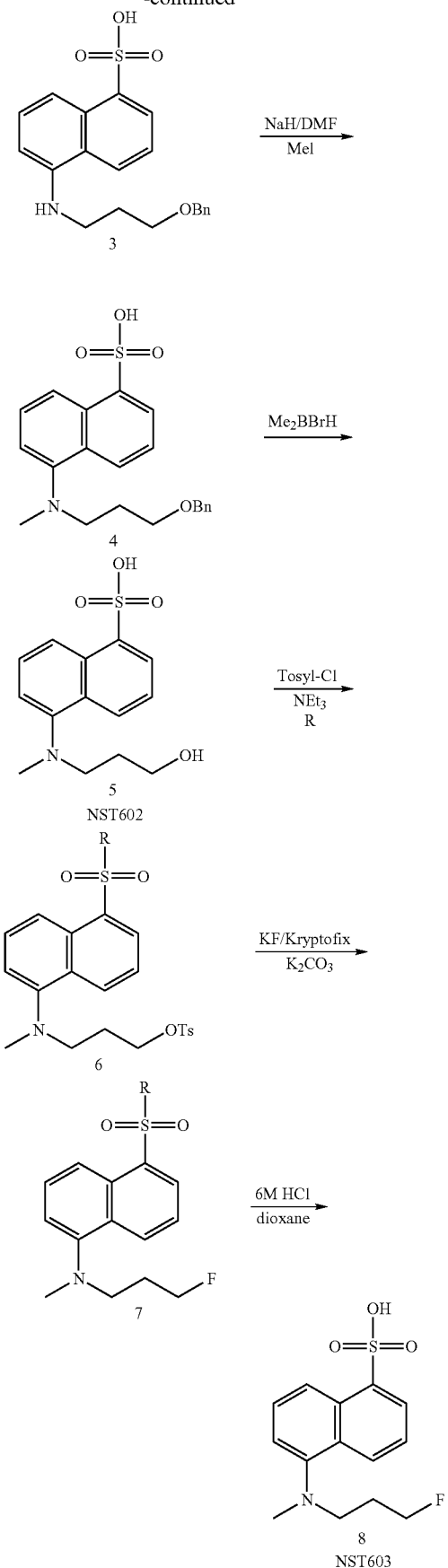

Example 15

Selective Binding of NST601 to Apoptotic HeLa Cells in vitro

HeLa S3 cells (ATCC CCL-2.2) were grown in Dulbecco's modified Eagle's medium (DMEM), supplemented with 2 mM of L-glutamine; 100 units/ml of penicillin; 100 µg/ml of streptomycin; 12.5 units/ml of nystatin and 10% of fetal calf serum (FCS). Cells were seeded at a density of $5 \times 10^6$ cells/plate, on a 10 cm$^3$ culture plates, in a volume of 10 ml, and were allowed to age by incubating the culture for 96 hours without exchange of the growth medium. As a result, a marked percentage of the cells became apoptotic. Cells were harvested using a cell scraper, separated to single cells by passage through a syringe with a 18 G needle, and re-suspended at a density of $10^6$ cells/ml in PBS buffer at pH=7.4. The selective binding of the NST601 compound to apoptotic cells was determined by flow cytometric (FACS) analysis using Becton-Dickinson cell sorter and CellQuest software (excitation was at 356 nm and emission was measured at 530 nm). The analysis shown in FIG. 10 describes the uptake of NST601 compound into the population of apoptotic cells.

Figure 10A:
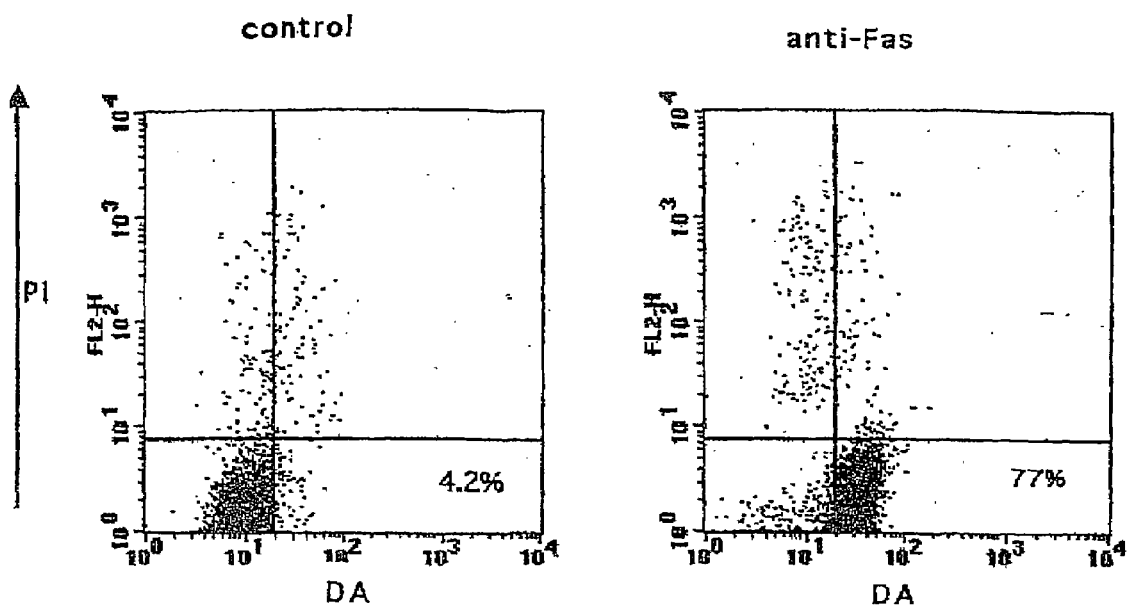
FIG. 10A is a dot plot showing the selective binding of NST601 upon induction of apoptosis.

As shown in the dot plot shown in FIG. 10A, the induction of apoptosis by the aging of the culture was associated with the emergence of a marked, distinct population of cells in the late stages of the apoptotic process, binding NST601 and occupying the right upper quadrant of the plot. The fraction of cells within the aged culture that bound NST601 represents the naturally occurring process of cell death due to deprivation of growth factors and acidification of the medium, typical for cells that are allowed to age in culture. Cells that do not undergo a process of cell death (occupying the lower left quadrant of the plot) remained non-stained.

Figure 10B:
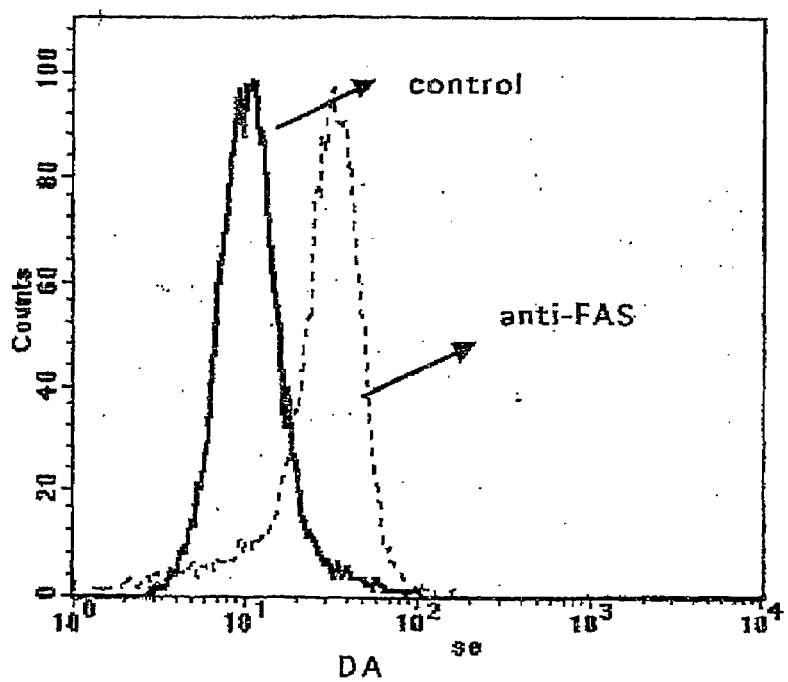
FIG. 10B is a histogram analysis of the data presented in FIG. 10A.

FIG. 10B is a histogram analysis of the data presented in FIG. 10A. The emergence of a distinct peak of highly fluorescent cells in the apoptotic process is clearly associated with aging of the culture. Therefore, NST601 can serve as a marker, which performs selective binding to apoptotic cells.

Example 16

Selective Binding of DA to Jurkat Cells Undergoing Apoptosis Induced by Anti-Fas Ab in vitro Cultured Jurkat cells (human adult T cell leukemia cells) were grown in suspension in RPMI medium (Beit-Haemek, Israel), supplemented with 10% of fetal calf serum (FCS), 2 mM of L-glutamine, 1 mM of sodium pyruvate, 1 mM 1 mM HEPES and antibiotics (100 units/ml penicilin; 100 µg/ml streptomycin and 12.5 units/ml of nystatin). Prior to induction of apoptosis, medium was replaced with HBS buffer (10 mM HEPES; 140 mM NaCl, 1 mM CaCl). Apoptosis was then triggered by treatment with anti-Fas Ab (0.1 µg/ml; 3 hrs). As a result, a marked percentage of the cells became apoptotic. Non-treated cells served as control. Both control cells and apoptotic cells were then incubated for 20 minutes with 250 µM of DA. Subsequently, cells were co-stained with propidium iodide (PI). Binding of DA to the control and apoptotic cells was determined by flow cytometric (FACS) analysis using Becton-Dickinson cell sorter and CellQuest software (excitation was at 356 nm and emission was measured at 530 nm). The analysis is shown in FIG. 11.

In the dot plot shown in FIG. 11A, the left lower quadrant represents the healthy, non-stained fraction of cells. The right lower quadrant represents the newly formed population of cells in the early stages of apoptosis. These cells still maintain membrane integrity and thus exclude PI. Cells binding both DA and PI, i.e., cells in the late stages of apoptosis are represented in the right upper quadrant.

The induction of apoptosis was associated with the emergence of a marked, distinct population of cells in the early stages of the apoptotic process, selectively binding DA and occupying the tight lower quadrant of the plot. The percent of identified early apoptotic events within the population is 77% in the apoptotic cells as compared with 4.2% of the non-treated control cells. FIG. 11B is a histogram analysis of the data presented in FIG. 11A. The emergence of a new and distinct peak of highly fluorescent cells in the early phase of the apoptotic process is clearly associated with anti-Fas treatment. Therefore, DA can serve as a marker, which performs selective binding to cells in early apoptosis.

Example 17

Synthetic Scheme for NST650

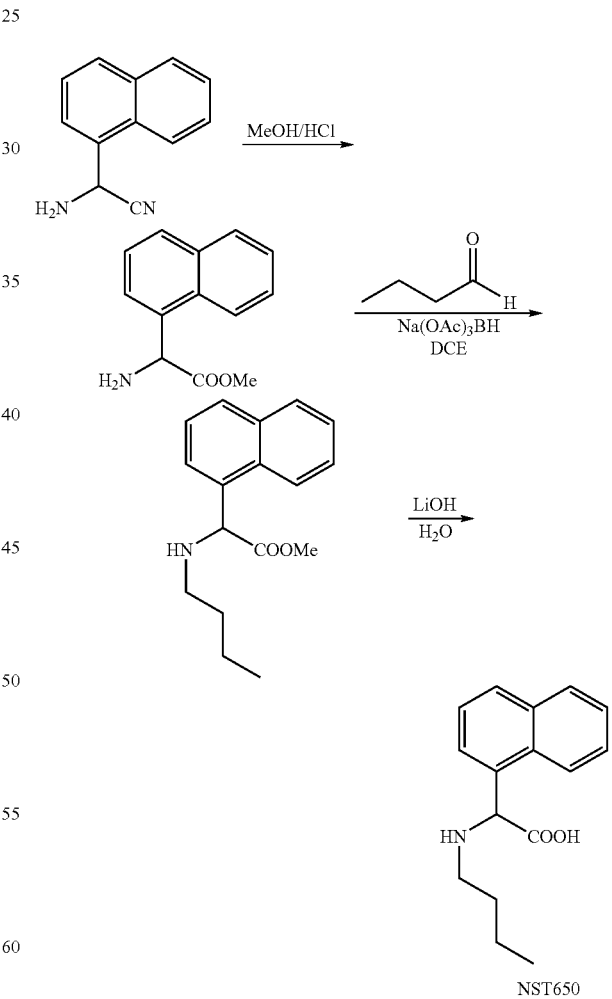

The invention claimed is:

1. A compound, represented by the structure as set forth in formula (VI):

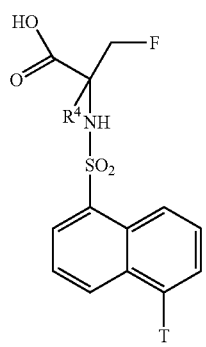

(VI)

wherein T is a —OH, —O—CH₃, —O—(CH₂)ᵧCH₃, NH₂, N(CH₃)₂, N[(CH₂)₃CH₃]₂, —N(CH₃)[(CH₂)₂CH₃], —N(CH₃)CH₂CH₃ or —N(CH₃)[(CH₂)₃CH₃]; wherein y stands for an integer of 1, 2, or 3; and R⁴ is hydrogen or a $C_1$, $C_2$, $C_3$, $C_4$, $C_5$ or $C_6$ straight or branched alkyl, and wherein the F atom is $^{18}F$ or $^{19}F$ or a mixture of fluorine isotopes.

2. A compound according to claim 1, represented by the structure as set forth in formula (VII):

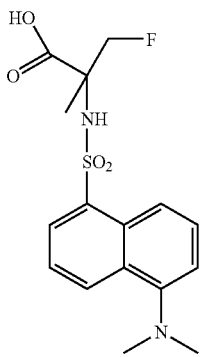

(VII)

wherein the F atom is $^{18}F$ or $^{19}F$ or a mixture of fluorine isotopes.

3. A compound according to claim 1, represented by the structure as set forth in formula (VIII):

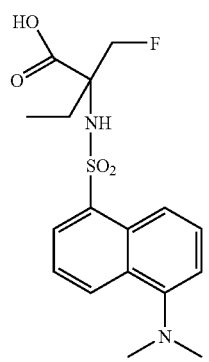

(VIII)

wherein the F atom is $^{18}F$ or $^{19}F$ or a mixture of fluorine isotopes.

4. A compound represented by the structure as set forth in formula (IX):

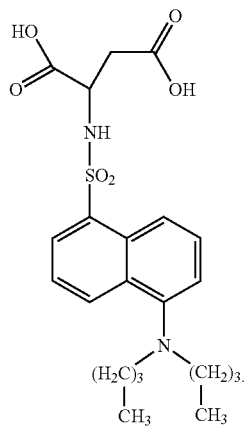

(IX)

5. A compound represented by the structure as set forth in formula (X):

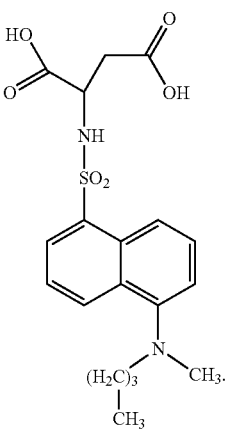

(X)

6. A compound represented by the structure as set forth in formula (XI):

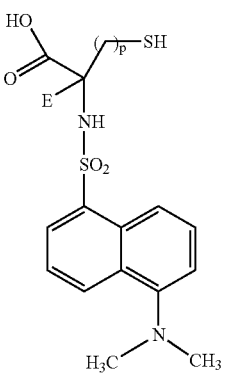

(XI)

wherein E is $C_1$, $C_2$, $C_3$ or $C_4$ alkyl; $C_1$, $C_2$, $C_3$ or $C_4$ fluoroalkyl; or $C_1$, $C_2$ $C_3$ or $C_4$ hydroxyalkyl; p stands for an integer of 1 or 2.

7. A compound according to claim 6, wherein p is 1.

8. A method for selective targeting of a chemical compound to a cell undergoing perturbation of the normal organization of its plasma membrane (PNOM-cell) present in a cell population, comprising the step of contacting the cell population with a perturbed membrane binding compound (PMBC), being a chemical compound represented by the structure set forth in formula (VIII) of claim 3, thereby selectively targeting the chemical compound to the PNOM-cells within the cell population.

9. A method of detecting the presence of PNOM-cells within a cell population selected from: a cell culture, a tissue in a human patient and a tissue in an animal, comprising the steps of:
   (i) administrating the cell population with a PMBC, or a conjugate comprising said PMBC and a marker for imaging, wherein said PMBC is represented by the structure set forth in formula (VIII) of claim 3; and
   (ii) determining the amount of PMBC bound to cells in the cell population wherein a bound amount which is significantly higher than a control indicates the presence of PNOM-cells within the cell population.

10. A method according to claim 8, wherein the PNOM-cell is a cell undergoing a death process, an apoptotic cell or an activated platelet.

11. A method for selective targeting of a PNOM-cell present in a cell population, comprising the step of:
   (i) contacting the cell population with a PMBC, or a conjugate comprising said PMBC and a marker for imaging, wherein said PMBC is represented by the structure set forth in formula (VIII) of claim 3; and
   (ii) determining the amount of PMBC bound to cells in said cell population, wherein a bound amount which is significantly higher than a control indicates the presence of said PNOM-cells within the cell population.

* * * * *